US010046028B2

(12) United States Patent
Gregory et al.

(10) Patent No.: US 10,046,028 B2
(45) Date of Patent: *Aug. 14, 2018

(54) METHODS AND COMPOSITIONS FOR MODULATING PD1

(71) Applicant: Sangamo BioSciences, Inc., Richmond, CA (US)

(72) Inventors: Philip D. Gregory, Richmond, CA (US); Michael C. Holmes, Richmond, CA (US); Matthew C. Mendel, Richmond, CA (US); Xiangdong Meng, Richmond, CA (US); David Paschon, Richmond, CA (US); Andreas Reik, Richmond, CA (US); Fyodor Urnov, Richmond, CA (US)

(73) Assignee: Sangamo Therapeutics, Inc., Richmond, CA (US)

( * ) Notice: Subject to any disclaimer, the term of this patent is extended or adjusted under 35 U.S.C. 154(b) by 63 days.

This patent is subject to a terminal disclaimer.

(21) Appl. No.: 15/133,862

(22) Filed: Apr. 20, 2016

(65) Prior Publication Data

US 2016/0220634 A1 Aug. 4, 2016

Related U.S. Application Data

(63) Continuation of application No. 14/039,828, filed on Sep. 27, 2013, now Pat. No. 9,402,879, which is a continuation of application No. 12/927,557, filed on Nov. 17, 2010, now Pat. No. 8,563,314, which is a continuation-in-part of application No. 12/284,887, filed on Sep. 25, 2008, now Pat. No. 9,506,120.

(60) Provisional application No. 60/995,566, filed on Sep. 27, 2007, provisional application No. 61/281,432, filed on Nov. 17, 2009.

(51) Int. Cl.
*A61K 38/17* (2006.01)
*C12N 9/22* (2006.01)
*A61K 35/17* (2015.01)

(52) U.S. Cl.
CPC .......... *A61K 38/1709* (2013.01); *A61K 35/17* (2013.01); *C12N 9/22* (2013.01); *C07K 2319/71* (2013.01)

(58) Field of Classification Search
CPC . A61K 48/00; C07K 2319/71; C07K 2319/81
See application file for complete search history.

(56) References Cited

U.S. PATENT DOCUMENTS

| | | | |
|---|---|---|---|
| 5,356,802 A | 10/1994 | Chandrasegaran | |
| 5,436,150 A | 7/1995 | Chandrasegaran | |
| 5,487,994 A | 1/1996 | Chandrasegaran | |
| 5,789,538 A | 8/1998 | Rebar et al. | |
| 5,925,523 A | 7/1999 | Dove et al. | |
| 6,007,988 A | 12/1999 | Choo et al. | |
| 6,013,453 A | 1/2000 | Choo et al. | |
| 6,140,081 A | 10/2000 | Barbas | |
| 6,140,466 A | 10/2000 | Barbas et al. | |
| 6,200,759 B1 | 3/2001 | Dove et al. | |
| 6,242,568 B1 | 6/2001 | Barbas et al. | |
| 6,410,248 B1 | 6/2002 | Greisman et al. | |
| 6,453,242 B1 | 9/2002 | Eisenberg et al. | |
| 6,479,626 B1 | 11/2002 | Kim et al. | |
| 6,479,653 B1* | 11/2002 | Natesan ............... | C07K 14/005 435/320.1 |
| 6,534,261 B1 | 3/2003 | Cox et al. | |
| 6,599,692 B1 | 7/2003 | Case et al. | |
| 6,607,882 B1 | 8/2003 | Cox, III et al. | |
| 6,808,710 B1 | 10/2004 | Wood et al. | |
| 6,824,978 B1 | 11/2004 | Cox, III et al. | |
| 6,903,185 B2 | 6/2005 | Kim et al. | |
| 6,933,113 B2 | 8/2005 | Case et al. | |
| 6,946,292 B2 | 9/2005 | Kanda et al. | |
| 6,979,539 B2 | 12/2005 | Cox, III et al. | |
| 7,013,219 B2 | 3/2006 | Case et al. | |
| 7,153,949 B2 | 12/2006 | Kim et al. | |
| 7,163,824 B2 | 1/2007 | Cox, III et al. | |
| RE42,211 E | 3/2011 | Choo et al. | |
| 8,034,598 B2 | 10/2011 | Miller | |
| 8,071,370 B2 | 12/2011 | Wolfee et al. | |
| 2002/0115215 A1* | 8/2002 | Wolfe ................ | C07K 14/4702 435/455 |
| 2003/0082552 A1* | 5/2003 | Wolfe .............. | C07K 14/43581 435/6.12 |
| 2003/0165997 A1 | 9/2003 | Kim et al. | |
| 2003/0232410 A1 | 12/2003 | Liljedahl et al. | |
| 2004/0002092 A1 | 1/2004 | Arnould et al. | |
| 2005/0026157 A1 | 2/2005 | Baltimore | |
| 2005/0064474 A1 | 3/2005 | Urnov et al. | |
| 2005/0208489 A1 | 9/2005 | Carroll | |
| 2006/0063231 A1 | 3/2006 | Li et al. | |
| 2006/0078552 A1 | 4/2006 | Arnould et al. | |
| 2006/0153826 A1 | 7/2006 | Arnould et al. | |
| 2006/0188987 A1 | 8/2006 | Guschan et al. | |
| 2006/0206949 A1 | 9/2006 | Arnould et al. | |
| 2007/0117128 A1 | 5/2007 | Smith et al. | |
| 2007/0134796 A1 | 6/2007 | Holmes et al. | |
| 2008/0131962 A1 | 6/2008 | Miller | |
| 2008/0159996 A1 | 7/2008 | Ando et al. | |
| 2009/0111119 A1 | 4/2009 | Doyon et al. | |
| 2009/0203140 A1 | 8/2009 | Amacher et al. | |

FOREIGN PATENT DOCUMENTS

GB 2338237 A 12/1999
WO WO 95/19431 A1 7/1995
(Continued)

OTHER PUBLICATIONS

Ginn et al. The Journal of Gene Medicine, vol. 15, pp. 65-77, 2013.*
(Continued)

*Primary Examiner* — Jennifer Dunston
(74) *Attorney, Agent, or Firm* — Pasternak Patent Law; Susan Abrahamson

(57) ABSTRACT

Disclosed herein are methods and compositions for modulating expression of a PD1 gene.

3 Claims, 7 Drawing Sheets

(56) References Cited

FOREIGN PATENT DOCUMENTS

| WO | WO 96/06166 A1 | 2/1996 | |
|---|---|---|---|
| WO | WO 98/37186 A1 | 8/1998 | |
| WO | WO 98/53057 A1 | 11/1998 | |
| WO | WO 98/53058 A1 | 11/1998 | |
| WO | WO 98/53059 A1 | 11/1998 | |
| WO | WO 98/53060 A1 | 11/1998 | |
| WO | WO 98/54311 A1 | 12/1998 | |
| WO | WO 00/27878 A1 | 5/2000 | |
| WO | WO 01/14557 A1 | 3/2001 | |
| WO | WO 01/60970 A2 | 8/2001 | |
| WO | WO 01/88197 A2 | 11/2001 | |
| WO | WO 02/16536 A1 | 2/2002 | |
| WO | WO 02/077227 A2 | 10/2002 | |
| WO | WO 02/099084 A2 | 12/2002 | |
| WO | WO 03/016496 A2 | 2/2003 | |
| WO | WO 03/016571 A1 | 2/2003 | |
| WO | WO 03/022875 A2 | 3/2003 | |
| WO | WO 03/078619 A1 | 9/2003 | |
| WO | WO 04/067753 A2 | 8/2004 | |
| WO | WO 05/014791 A2 | 2/2005 | |
| WO | WO 05/084190 A2 | 9/2005 | |
| WO | WO 06/097853 A1 | 9/2006 | |
| WO | WO 07/014275 A2 | 1/2007 | |
| WO | WO 07/014181 A2 | 2/2007 | |
| WO | WO 07/049095 A1 | 5/2007 | |
| WO | WO 07/139898 A2 | 12/2007 | |
| WO | WO-2008011344 A2 * | 1/2008 | ........... A61K 38/177 |
| WO | WO 09/042163 A2 | 4/2009 | |
| WO | WO 11/097036 A1 | 8/2011 | |

OTHER PUBLICATIONS

Chira et al. Oncotarget, vol. 6, No. 31, pp. 30675-30703, Sep. 2015.*

Wang et al. Membrane estrogen receptor regulates experimental autoimmune encephalomyelitis through up-regulation of programmed death 1. The Journal of Immunology, vol. 182, pp. 3294-3303, 2008.*

Francisco et al. The PD-1 pathway in tolerance and autoimmunity. Immunological Reviews, vol. 236, pp. 219-242, Jul. 2010.*

Cuddapah et al. Global analysis of the insulator binding protein CTCF in chromatin barrier regions reveals demarcation fo active and repressive domains. Genome Research, vol. 19, No. 1, pp. 24-32, Jan. 2009.*

Deuring et al. The ISWI chromatin-remodeling protein is required for gene expression and maintenance of higher order chromatin structure in vivo. Molecular Cell, vol. 5, pp. 355-365, Feb. 2000.*

Burgio et al. Genetic identification of a network of factors that functionally interact with the nucleosome remodeling ATPase ISWI. PLoS Genetics, vol. 4, No. 6, e1000089, Jun. 2008.*

Prokunina et al. A regulatory polymorphism in PDCD1 is associated with susceptibility to systemic lups erythematosus in humans. Nature Genetics, vol. 32, pp. 666-669, Dec. 2002. (Year: 2002).*

Bertsias et al. Genetic, immunologic, and immunohistochemical analysis of the programmed death 1/programmed death ligand 1 pathway in human systemic lupus erythematosus. Arthritis & Rheumatism, vol. 60, No. 1, pp. 207-218, Jan. 2009. (Year: 2009).*

Angharad, et al., "Beyond the Antigen Receptor: Editing the Genome of T-Cells for Cancer Adoptive Cellular Therapies," *Frontiers in Immunology*, 4(1): XPO55110101, doi: 10.3389/fimmu. 2013.00221.

Arnould, et al., "Engineering of Large Numbers of Highly Specific Homing Endonucleases That Induce Recombination on Novel DNA Targets," *J. Mol. Biol.* 355:443-458 (2006).

Beerli, et al., "Engineering Polydactyl Zinc-Finger Transcription Factors," *Nature Biotechnology* 20:135-141 (2002).

Chames, et al., "In Vivo Selection of Engineered Homing Endonucleases Using Double-Strand Break Induced Homologous Recombination," *Nucleic Acids Research* 33(20):e178 (2005).

Choo, et al., "Advances in Zinc Finger Engineering," *Curr. Opin. Struct. Biol.* 10:411-416 (2000).

Dotti, "Blocking PD-1 in Cancer Immunotherapy,"*Blood* 114:1457-1458 (2009).

Drier, et al., "Development of Zinc Finger Domains for Recognition of the 5'-ANN-3' Family of DNA Sequences and Their Use in the Construction of Artificial Transcription Factors," *The Journal of Biological Chemistry* 276(31):29466-29478 (2001).

Drier, et al., "Development of Zinc Finger Domains for Recognition of the 5'-ANN-3' Family DNA Sequence and Their Use in the Construction of Artificial Transcription Factors," *The Journal of Biological Chemistry* 280:35588-35597 (2005).

Durai, et al., "Zinc Finger Nucleases: Custom-Designed Molecuar Scissors for Genome Engineering of Plant and Mammalian Cells," *Nucleic Acids Research* 33(18):5978-5990 (2005).

Edelstein, et al. "Gene therapy clinical trials worldwide 1989-2004—An overview," *J. Gene Med.* 6:597-602 (2004).

Finger, et al., "The Human PD-1 Gene: Complete CDNA, Genomic Organization, and Developmentally Regulated Expression in B Cell Progenitors," *Gene* 197:177-187 (1997).

Fishman-Lobell, et al., "Removal of Nonhomologous DNA Ends in Double-Strand Break Recombination: The Role of the Yeast Ultraviolet Repair Gene RAD1," *Science* 258:480-484 (1992).

Genbank Accession No. U64863.1 (Oct. 12, 2005) 3 pages.

Isalan, et al., "A Rapid, Generally Applicable Method to Engineer Zinc Fingers Illustrated by Targeting the HIV-1 Promoter," *Nat. Biotechnol.* 19:656-660 (2001).

Kandavelou, et al., "Magic Scissors for Genome Surgery," *Nature Biotechnology* 23:686-687 (2005).

Klug, et al., "Towards Therapeutic Applications of Engineered Zinc Finger Proteins," *FEBS Letters* 892-894 (2005).

Kim, et al., "Hybrid Restriction Enzymes: Zinc Finger Fusions to FOK I Cleavage Domain,"*PNAS USA* 93:1156-1160 (1996).

Luo, et al. "Synthetic DNA delivery systems," *Nature Biotechnology*, 18:33-37 (2000).

Mao and Wu, "Inhibitory RNA Molecules in Immunotherapy for Cancer," *Methods Mol. Biol.* 623:325-339 (2010).

Miller, et al., "An Improved Zinc-Finger Nuclease Architecture for Highly Specific Genome Editing," *Nat. Biotechnology* 25:778-785 (2007).

Moehle, et al., "Targeted Gene Addition Into a Specified Location in the Human Genome Using Designed Zinc Finger Nucleases," *PNAS USA* 104:3055-3060 (2007).

Nishimura et al. "Development of Lupus-Like Autoimmune Diseases by Disruption of the PD-1 Gene Encoding an ITIM Motif-Carrying Immunoreceptor," *Immunity*, 11:141-151 (1999).

Okazaki and Honjo, "PD-1 and PD-1 Ligands: From Discovery to Clinical Application," *International Immunology* 19(7):813-824.

Pabo, et al., "Design and Selection of Novel CYS2-HIS2 Zinc Finger Proteins," *Ann. Rev. Biochem.* 70:313-340 (2001).

Palu et al. "In pursuit of new developments for gene therapy for human diseases," *J. Biotechnol.* 68:1-13 (1999).

Paques, et al., "Two Pathways for Removal of Nonhomologous DNA Ends During Double-Strand Break Repair in *Saccharomyces cerevisiae,"* *Molecular and Cellular Biology* 17:6765-6771 (1997).

Rudin, et al., "Genetic and Physical Analysis of Double-Strand Break Repair and Recombination in *Saccharomyces cerevisiae,"* *Genetics* 122: 519-534 (1989).

Segal, et al., "Custom DNA-Binding Proteins Come of Age: Polydactyl Zinc-Finger Proteins," *Curr. Opin. Biotechnol.* 12:632-637 (2001).

Segal, et al., "Evaluation of Modular Strategy for the Construction of Novel Polydactyl Zinc Finger DNA-Binding Proteins," *Biochemistry* 42:2137-2148 (2003).

Sester, et al., "PD-1 Expression and IL-2 Loss of Cytomegalovirus-Specific T-Cells Correlates With Viremia and Reversible Functional Anergy," *American Journal of Transplantation* 8(7):1486-1497 (2008).

Urnov, et al., "Highly Efficient Endogenous Human Gene Correction Using Designed Zinc-Finger Nucleases," *Nature* 435:646-651 (2005).

Verma, et al. "Gene Therapy—Promises, Problems and Prospects," *Nature* 389:239-242 (1997).

(56) References Cited

OTHER PUBLICATIONS

Verma and Weitzman, "Gene Therapy: Twenty-First Century Medicine," *Annual Review of Biochemistry* 74:11-738 (2005).
Waldmann, "Effective Cancer Therapy Through Immunomodulation," *Annual Review of Medicine* 57:65-81 (2006).
Wong et al., "Programmed Death-1 Blockade Enhances Expansion And Functional Capacity of Human Melanoma Antigen-Specific CTLs," *International Immunology* 19(10):1223-1334 (2007).

* cited by examiner

Figure 2

```
                    ***********    ******************    (*= ZFN binding sites)
          ggctgctccaggcatgcagatcccacaggcgccctggcccagtcgtgccggtgctacaactggctggcggcc   WT PD1

Insertions:
1    ggctgctccaggcatgcagatcccacaggcgccctgCccagtcgtctgggcggtgctacaactggctggcggc   +1
3    ggctgctccaggcatgcagatcccacaggcgccctgGggccagtcgtctgggcggtgctacaactggctggcggc  +1
1    ggctgctccaggcatgcagatcccacaggcgccctgccAagtcgtctgggcggtgctacaactggctggcggc   +1
4    ggctgctccaggcatgcagatcccacaggcgccctgGggccagtcgtctgggcggtgctacaactggctggcggc  +1
1    ggctgctccaggcatgcagatcccacaggcgccctgccAagtcgtctgggcggtgctacaactggctggcggc   +1
2    ggctgctccaggcatgcagatcccacaggcgccctGGCCAggccagtcgtctgggcggtgctacaactggctggc  +5
1    ggctgctccaggcatgcagatcccacaggcgccctgGCCAggccagtcgtctgggcggtgctacaactggctgc   +4
2    ggctgctccaggcatgcagatcccacaggcgccctGGGCCAggccagtcgtctgggcggtgctacaactggctgg  +5
1    ggctgctccaggcatgcagatcccacaggcgccctggGCccagtcgtctgggcggtgctacaactggctgcgg   +2
1    ggctgctccaggcatgcagatcccacaggcgccctggccAagtcgtctgggcggtgctacaactggctggcggc  +1
1    ggctgctccaggcatgcagatcccacaggcgccctggccCccagtcgtctgggcggtgctacaactggctggcggc +1
1    ggctgctccaggcatgcagatcccacaggcgccctGGCCcagccctgggccagtcgtctgggcggtgctacaactggctggc +4
1    ggctgctccaggcatgcagatcccacaTcaggcgccctggccagtcgtctgggcggtgctacaactggctggcggc +1
4    ggctgctccaggcatgcagatcccacaggcgccctGggccagtcgtctgggcggtgctacaactggctggcggc   +1

Deletions:
1    ggctgctccaggcatgcagatcccacaggcgcc-----------tcgtctgggcggtgctacaactggctggcggcc   -7
1    ggctgctccaggcatgcagat----------------------gtctggcggtgctacaactggctggcggcc    -22
1    ggctgctccaggcatgcagatcccacagg-------------cgtctgggcggtgctacaactggctggcggcc   -13
1    ggc-----------------------------------------------tgctacaactggctggcggcc      -50
1    ggctgctccaggcatgcagatcccaca-------------------ctacaactggctggcggcc           -19
1    ggctgctccaggcatgcagatcccaca-----------------gggcggtgctacaactggctggcggcc     -20
1    ggctgctccaggcatgcagatcccacaggc-------------cagtcgtctgggcggtgctacaactggctggcggcc -13
1    ggctgctccaggcatgcagatcccacagg---------------cgtctgggcggtgctacaactggctggcggcc -13
1    ggctgctccaggcatgcagatcccacaggcgccc-ggccagtc--cctgcggtgctacaactggctggcggcc   -1
1    ggctgctccaggcatgcagatcccacaggcg-cctgccagtc-ccagtcgtctgggcggtgctacaactggctggcggcc -1
2    ggctgctccaggcatg-----------cagtcgtctgggcggtgctacaactggctggcggcc             -22
1    ggctgctccaggcatgcagatgcagatgcagatgcagg-------cgtctgggcggtgctacaactggctggcggcc -13
1    ggctgctccaggcatgcagatgcagg------------gccagtcgtctgggcggtgctacaactggctggcggcc -1
1    ggctgctccaggcatgcagat--------------ccagtcgtctgggcggtgctacaactggctggcggcc    -16
```

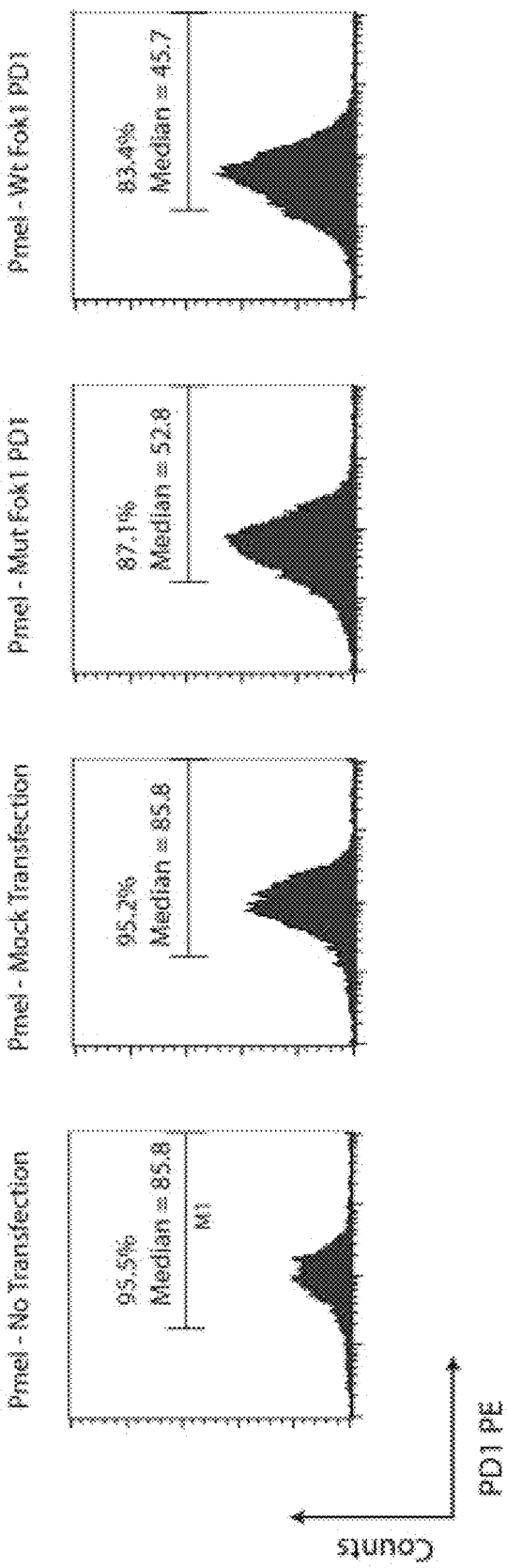
Figure 3: Transfection of Pmel T cells with either Mut Fok1 or WT Fok1 DNA decreases the expression of PD1 upon anti-CD3 stimulation

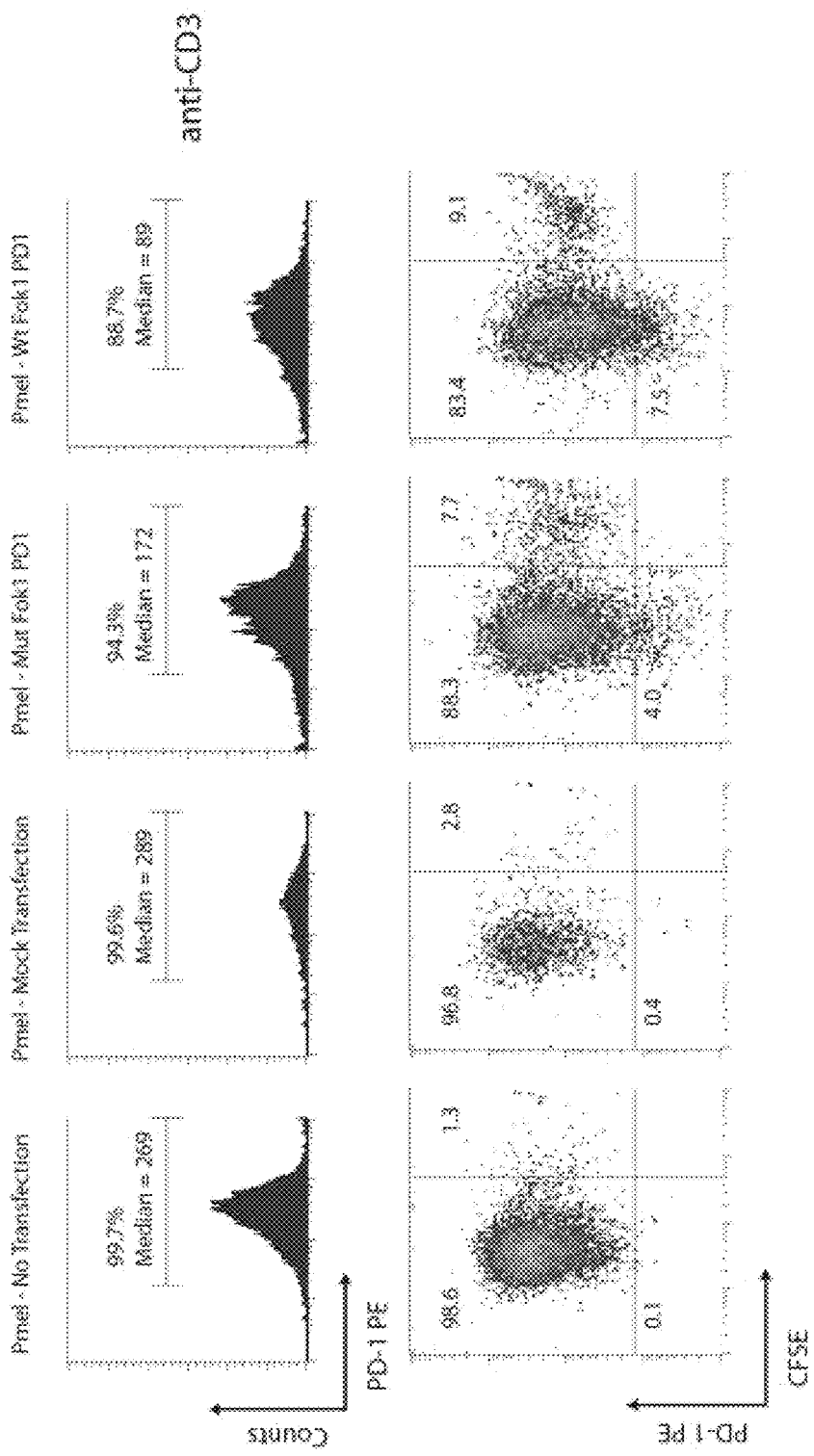

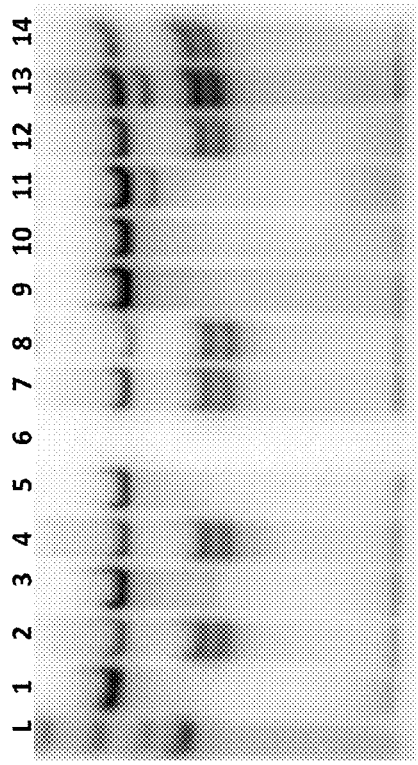

| Sample # | Sample contents | % NHEJ |
|---|---|---|
| 1 | CCR5 ZFNs, 1st stimulation | 0 |
| 2 | PD1 ZFNs, 1st stimultion | 41.8 |
| 3 | CCR5 ZFNs, 2nd stimulation before sorting | 0 |
| 4 | PD1 ZFNs, 2nd stimulation before sorting | 42.6 |
| 5 | CCR5 ZFNs, 2nd stimulation, after sorting for PD1+ CD25+ | 0 |
| 6 | CCR5 ZFNs, 2nd stimulation, after sorting for PD1- CD25+ | 0 |
| 7 | PD1 ZFNs, 2nd stimulation, after sorting for PD1+ CD25+ | 36.6 |
| 8 | PD1 ZFNs, 2nd stimulation, after sorting for PD1- CD25+ | 56.4 |
| 9 | CCR5 ZFNs, 2nd stimulation, PD1+ bead purification | 0 |
| 10 | CCR5 ZFNs, 2nd stimulation, PD1-, CD25 bead purification | 0 |
| 11 | CCR5 ZFNs, 2nd stimulation, PD1-, CD25- bead purification | 0 |
| 12 | PD1 ZFNs, 2nd stimulation, PD1+ bead purification | 29.6 |
| 13 | PD1 ZFNs, 2nd stimulation, PD1-, CD25+ bead purification | 42 |
| 14 | PD1 ZFNs, 2nd stimulation, PD1-, CD25- bead purification | 48 |

Figure 6

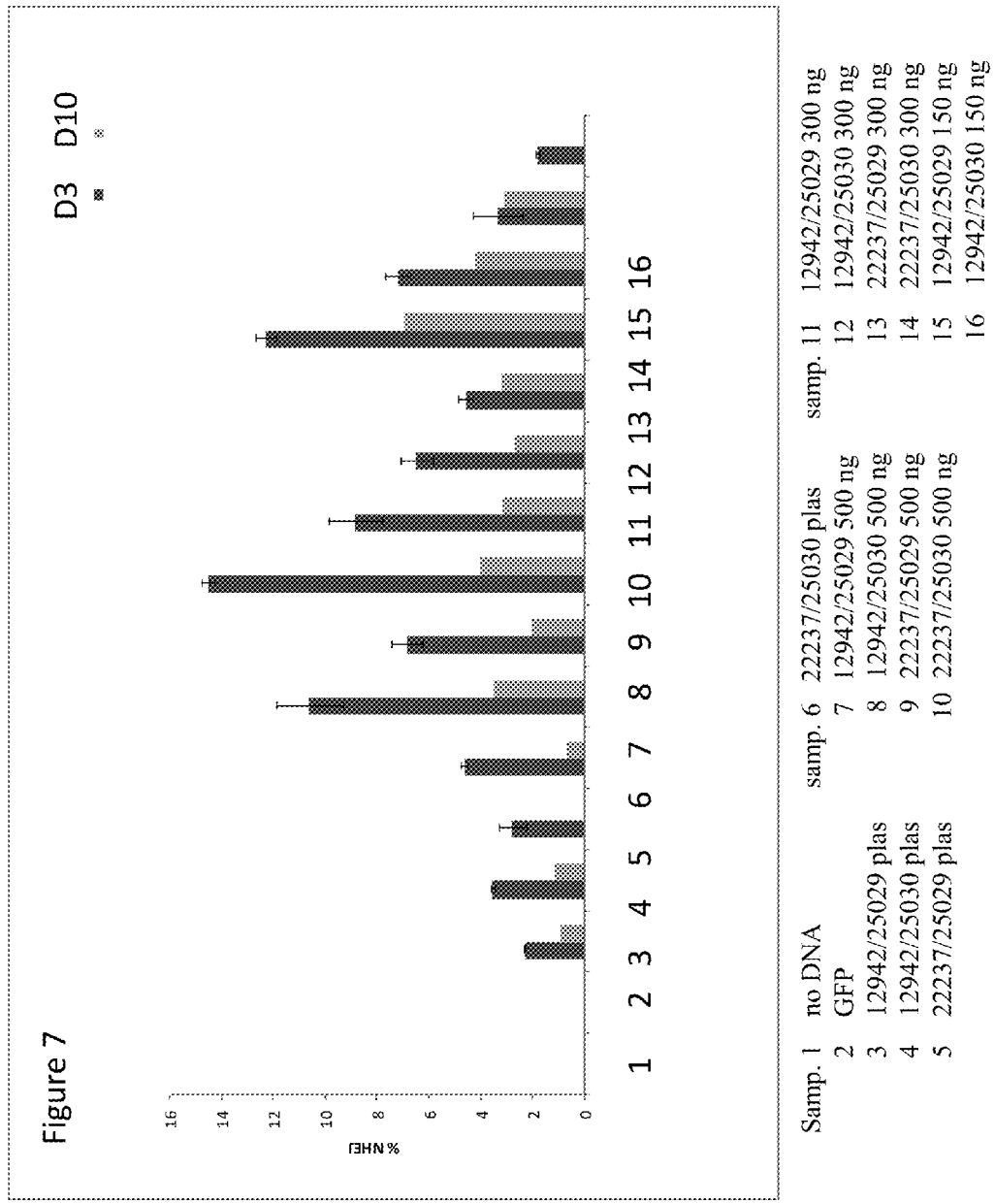

SEQUENCE LISTING

```
<160> NUMBER OF SEQ ID NOS: 110

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gln Ser Gly His Leu Ser Arg
1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Ser Asp Ser Leu Ser Val
1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

His Asn Asp Ser Arg Lys Asn
1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 4

Arg Ser Asp Asp Leu Thr Arg
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Ser Asp His Leu Thr Gln
1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Ser Ala Ala Leu Ser Arg
1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Ser Asp His Leu Thr Thr
1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Asp Arg Ser Ala Leu Ser Arg
1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Asp Arg Ser Ala Leu Ala Arg
1               5

<210> SEQ ID NO 10

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Ser Ala Ala Leu Ala Arg
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Arg Ser Asp Asp Leu Ser Lys
1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Arg Asn Asp His Arg Lys Asn
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Arg Ser Asp His Leu Ser Glu
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Thr Ser Ser Asp Arg Thr Lys
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15
```

```
Gln Ser Ala Ser Arg Lys Asn
1               5
```

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

```
Arg Ser Asp Val Leu Ser Glu
1               5
```

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

```
Arg Ser Ala Asn Leu Thr Arg
1               5
```

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

```
Arg Ser Asp His Leu Ser Gln
1               5
```

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

```
Thr Ser Ser Asn Arg Lys Thr
1               5
```

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

```
Asp Arg Ser Asn Leu Ser Arg
1               5
```

<210> SEQ ID NO 21
<211> LENGTH: 7
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 21

Arg Ser Asp Ala Leu Ala Arg
1               5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Asp Asp Trp Asn Leu Ser Gln
1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Arg Ser Ser Ala Leu Ser Arg
1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Arg Pro Leu Ala Leu Lys His
1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Thr Arg Pro Val Leu Lys Arg
1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Arg Ala Asn Ser Leu Leu Arg
1               5
```

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Arg Pro Ser Thr Leu His Arg
1               5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Arg Ser Asp Glu Leu Thr Arg
1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Arg Asn Asn Asn Leu Arg Thr
1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Thr Asn Trp His Leu Arg Thr
1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Arg Thr Pro His Leu Thr Leu
1               5

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Arg Ser Ala Gln Leu Ala Thr
1               5

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Arg Cys Thr His Leu Tyr Leu
1               5

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Arg Pro Thr Gln Arg Tyr Ser
1               5

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Arg Ala Asn His Arg Glu Cys
1               5

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Arg Lys Phe Ala Arg Pro Ser
1               5

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Arg Asn Phe Ser Arg Ser Asp
1               5

<210> SEQ ID NO 38
<211> LENGTH: 7
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 38

His Pro His His Arg Met Cys
1               5

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Arg Met Gly Arg Leu Ser Thr
1               5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Arg His Ser Arg Leu Thr Thr
1               5

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Thr Arg Pro Val Leu Met Arg
1               5

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Arg Ala Asn His Arg Val Cys
1               5

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Arg Ser Thr His Leu Leu Gly
1               5
```

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Arg Ser Cys Gly Leu Trp Ser
1               5

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Arg Asn Ala Ala Leu Thr Arg
1               5

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Cys Asn Ala Ala Leu Thr Arg
1               5

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Arg Glu Glu His Arg Ala Thr
1               5

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Arg His His His Leu Ala Ala
1               5

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 49

Arg Pro Met His Leu Thr Asn
1               5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Arg Ser Pro His Leu Tyr His
1               5

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Arg Cys Glu Ala Leu His His
1               5

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Asp Arg Ser Ala Gln Ala Arg
1               5

<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Arg Leu Pro Ala Leu Leu Ser
1               5

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

His Asn Ala Ala Leu Thr Arg
1               5

<210> SEQ ID NO 55
<211> LENGTH: 7
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 55

Arg Thr Tyr Asn Arg Thr Gln
1               5

<210> SEQ ID NO 56
<211> LENGTH: 28
<212> TYPE: DNA
<213> ORGANISM: Homo sapiens

<400> SEQUENCE: 56
ccagggcgcc tgtgggatct gcatgcct                                          28

<210> SEQ ID NO 57
<211> LENGTH: 28
<212> TYPE: DNA
<213> ORGANISM: Homo sapiens

<400> SEQUENCE: 57
cagtcgtctg ggcggtgcta caactggg                                          28

<210> SEQ ID NO 58
<211> LENGTH: 28
<212> TYPE: DNA
<213> ORGANISM: Homo sapiens

<400> SEQUENCE: 58
gaacacaggc acggctgagg ggtcctcc                                          28

<210> SEQ ID NO 59
<211> LENGTH: 28
<212> TYPE: DNA
<213> ORGANISM: Homo sapiens

<400> SEQUENCE: 59
ctgtggacta tggggagctg gatttcca                                          28

<210> SEQ ID NO 60
<211> LENGTH: 19
<212> TYPE: DNA
<213> ORGANISM: Homo sapiens

<400> SEQUENCE: 60
cagtcgtctg ggcggtgct                                                    19

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Thr Ser Gly Ser Leu Ser Arg
1               5

<210> SEQ ID NO 62
<211> LENGTH: 7
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 62

Gln Ser Gly Asp Leu Thr Arg
1               5

<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gln Ser Ser Asp Leu Arg Arg
1               5

<210> SEQ ID NO 64
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Gln Ser Ser His Leu Thr Arg
1               5

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Arg Ser Asp Asn Leu Arg Glu
1               5

<210> SEQ ID NO 66
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Arg Ser Asp Ser Leu Ser Lys
1               5

<210> SEQ ID NO 67
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Arg Ser Asp Asn Leu Ser Glu
1               5
```

<210> SEQ ID NO 68
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Glu Arg Ala Asn Arg Asn Ser
1               5

<210> SEQ ID NO 69
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Asp Arg Ser Asp Leu Ser Arg
1               5

<210> SEQ ID NO 70
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Asp Arg Ser His Leu Ala Arg
1               5

<210> SEQ ID NO 71
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Arg Ser Asp Asp Leu Ser Arg
1               5

<210> SEQ ID NO 72
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gln Ser Ala Asn Arg Thr Lys
1               5

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 73

Arg Ser Asp Thr Leu Ser Glu
1               5

<210> SEQ ID NO 74
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ala Asn Ser Asn Arg Ile Lys
1               5

<210> SEQ ID NO 75
<211> LENGTH: 28
<212> TYPE: DNA
<213> ORGANISM: Mus musculus

<400> SEQUENCE: 75
gtgctgcagt tgagctggca atcagggt                                           28

<210> SEQ ID NO 76
<211> LENGTH: 28
<212> TYPE: DNA
<213> ORGANISM: Mus musculus

<400> SEQUENCE: 76
cccaagtgaa tgaccagggt acctgccg                                           28

<210> SEQ ID NO 77
<211> LENGTH: 28
<212> TYPE: DNA
<213> ORGANISM: Mus musculus

<400> SEQUENCE: 77
cagctgccca acaggcatga cttccaca                                           28

<210> SEQ ID NO 78
<211> LENGTH: 28
<212> TYPE: DNA
<213> ORGANISM: Mus musculus

<400> SEQUENCE: 78
atgatctgga agcgggcatc ctggacgg                                           28

<210> SEQ ID NO 79
<211> LENGTH: 9
<212> TYPE: PRT
<213> ORGANISM: Unknown
<220> FEATURE:
<223> OTHER INFORMATION: Description of Unknown: Meganuclease motif
      sequence

<400> SEQUENCE: 79

Leu Ala Gly Leu Ile Asp Ala Asp Gly
1               5

<210> SEQ ID NO 80
<211> LENGTH: 7
<212> TYPE: PRT
<213> ORGANISM: Homo sapiens
```

<400> SEQUENCE: 80

Gln Ser Ala Asn Arg Thr Thr
1               5

<210> SEQ ID NO 81
<211> LENGTH: 75
<212> TYPE: DNA
<213> ORGANISM: Homo sapiens

<400> SEQUENCE: 81
ggctgctcca ggcatgcaga tcccacaggc gccctggcca gtcgtctggg cggtgctaca      60
actgggctgg cggcc                                                      75

<210> SEQ ID NO 82
<211> LENGTH: 75
<212> TYPE: DNA
<213> ORGANISM: Homo sapiens

<400> SEQUENCE: 82
ggctgctcca ggcatgcaga tcccacaggc gccctggccc agtcgtctgg gcggtgctac      60
aactgggctg gcggc                                                      75

<210> SEQ ID NO 83
<211> LENGTH: 75
<212> TYPE: DNA
<213> ORGANISM: Homo sapiens

<400> SEQUENCE: 83
ggctgctcca ggcatgcaga tcccacaggc gccctgggcc agtcgtctgg gcggtgctac      60
aactgggctg gcggc                                                      75

<210> SEQ ID NO 84
<211> LENGTH: 75
<212> TYPE: DNA
<213> ORGANISM: Homo sapiens

<400> SEQUENCE: 84
ggctgctcca ggcatgcaga tcccacaggc gccctggcca agtcgtctgg gcggtgctac      60
aactgggctg gcggc                                                      75

<210> SEQ ID NO 85
<211> LENGTH: 75
<212> TYPE: DNA
<213> ORGANISM: Homo sapiens

<400> SEQUENCE: 85
ggctgctcca ggcatgcaga tcccacaggc gccctgggcc agtcgtctgg gcggtgctac      60
aactgggctg gcggc                                                      75

<210> SEQ ID NO 86
<211> LENGTH: 75
<212> TYPE: DNA
<213> ORGANISM: Homo sapiens

<400> SEQUENCE: 86
ggctgctcca ggcatgcaga tcccacaggc gccctggcca agtcgtctgg gcggtgctac      60
aactgggctg gcggc                                                      75

<210> SEQ ID NO 87

<210> SEQ ID NO 87
<211> LENGTH: 75
<212> TYPE: DNA
<213> ORGANISM: Homo sapiens

<400> SEQUENCE: 87
ggctgctcca ggcatgcaga tcccacaggc gccctggcca ggccagtcgt ctgggcggtg    60
ctacaactgg gctgg                                                    75

<210> SEQ ID NO 88
<211> LENGTH: 75
<212> TYPE: DNA
<213> ORGANISM: Homo sapiens

<400> SEQUENCE: 88
ggctgctcca ggcatgcaga tcccacaggc gccctggcca gccagtcgtc tgggcggtgc    60
tacaactggg ctggc                                                    75

<210> SEQ ID NO 89
<211> LENGTH: 75
<212> TYPE: DNA
<213> ORGANISM: Homo sapiens

<400> SEQUENCE: 89
ggctgctcca ggcatgcaga tcccacaggc gccctggcca ggccagtcgt ctgggcggtg    60
ctacaactgg gctgg                                                    75

<210> SEQ ID NO 90
<211> LENGTH: 75
<212> TYPE: DNA
<213> ORGANISM: Homo sapiens

<400> SEQUENCE: 90
ggctgctcca ggcatgcaga tcccacaggc gccctgggcc cagtcgtctg gcggtgcta    60 caactgggct ggcgg                                                    75

<210> SEQ ID NO 91
<211> LENGTH: 75
<212> TYPE: DNA
<213> ORGANISM: Homo sapiens

<400> SEQUENCE: 91
ggctgctcca ggcatgcaga tcccacaggc gccctggcca agtcgtctgg gcggtgctac    60
aactgggctg gcggc                                                    75

<210> SEQ ID NO 92
<211> LENGTH: 75
<212> TYPE: DNA
<213> ORGANISM: Homo sapiens

<400> SEQUENCE: 92
ggctgctcca ggcatgcaga tcccacaggc gccctggccc agtcgtctgg gcggtgctac    60
aactgggctg gcggc                                                    75

<210> SEQ ID NO 93
<211> LENGTH: 75
<212> TYPE: DNA
<213> ORGANISM: Homo sapiens

<400> SEQUENCE: 93
ggctgctcca ggcatgcaga tcccacaggc gccctggccg gccagtcgtc tgggcggtgc    60

```
tacaactggg ctggc                                                      75

<210> SEQ ID NO 94
<211> LENGTH: 75
<212> TYPE: DNA
<213> ORGANISM: Homo sapiens

<400> SEQUENCE: 94
ggctgctcca ggcatgcaga tcccatcagg cgccctggcc agtcgtctgg gcggtgctac    60
aactgggctg gcggc                                                      75

<210> SEQ ID NO 95
<211> LENGTH: 75
<212> TYPE: DNA
<213> ORGANISM: Homo sapiens

<400> SEQUENCE: 95
ggctgctcca ggcatgcaga tcccacaggc gccctgggcc agtcgtctgg gcggtgctac    60
aactgggctg gcggc                                                      75

<210> SEQ ID NO 96
<211> LENGTH: 68
<212> TYPE: DNA
<213> ORGANISM: Homo sapiens

<400> SEQUENCE: 96
ggctgctcca ggcatgcaga tcccacaggc gccctcgtct gggcggtgct acaactgggc    60
tggcggcc                                                              68

<210> SEQ ID NO 97
<211> LENGTH: 53
<212> TYPE: DNA
<213> ORGANISM: Homo sapiens

<400> SEQUENCE: 97
ggctgctcca ggcatgcaga tgtctgggcg gtgctacaac tgggctggcg gcc            53

<210> SEQ ID NO 98
<211> LENGTH: 62
<212> TYPE: DNA
<213> ORGANISM: Homo sapiens

<400> SEQUENCE: 98
ggctgctcca ggcatgcaga tcccacaggc gtctgggcgg tgctacaact gggctggcgg    60
cc                                                                    62

<210> SEQ ID NO 99
<211> LENGTH: 25
<212> TYPE: DNA
<213> ORGANISM: Homo sapiens

<400> SEQUENCE: 99
ggctgctaca actgggctgg cggcc                                           25

<210> SEQ ID NO 100
<211> LENGTH: 56
<212> TYPE: DNA
<213> ORGANISM: Homo sapiens

<400> SEQUENCE: 100
```
ggctgctcca ggcatgcaga tcccacaggc gccctgctac aactgggctg gcggcc     56

<210> SEQ ID NO 101
<211> LENGTH: 55
<212> TYPE: DNA
<213> ORGANISM: Homo sapiens

<400> SEQUENCE: 101
ggctgctcca ggcatgcaga tcccacaggg cggtgctaca actgggctgg cggcc      55

<210> SEQ ID NO 102
<211> LENGTH: 62
<212> TYPE: DNA
<213> ORGANISM: Homo sapiens

<400> SEQUENCE: 102
ggctgctcca ggcatgcaga tcccacagtc gtctgggcgg tgctacaact gggctggcgg    60
cc                                                                  62

<210> SEQ ID NO 103
<211> LENGTH: 62
<212> TYPE: DNA
<213> ORGANISM: Homo sapiens

<400> SEQUENCE: 103
ggctgctcca ggcatgcaga tcccacaggc gtctgggcgg tgctacaact gggctggcgg    60
cc                                                                  62

<210> SEQ ID NO 104
<211> LENGTH: 74
<212> TYPE: DNA
<213> ORGANISM: Homo sapiens

<400> SEQUENCE: 104
ggctgctcca ggcatgcaga tcccacaggc gcccggccag tcgtctgggc ggtgctacaa    60
ctgggctggc ggcc                                                     74

<210> SEQ ID NO 105
<211> LENGTH: 74
<212> TYPE: DNA
<213> ORGANISM: Homo sapiens

<400> SEQUENCE: 105
ggctgctcca ggcatgcaga tcccacaggc gcctggccag tcgtctgggc ggtgctacaa    60
ctgggctggc ggcc                                                     74

<210> SEQ ID NO 106
<211> LENGTH: 74
<212> TYPE: DNA
<213> ORGANISM: Homo sapiens

<400> SEQUENCE: 106
ggctgctcca ggcatgcaga tcccacaggc gccctgccag tcgtctgggc ggtgctacaa    60
ctgggctggc ggcc                                                     74

<210> SEQ ID NO 107
<211> LENGTH: 53
<212> TYPE: DNA
<213> ORGANISM: Homo sapiens

<400> SEQUENCE: 107

```
ggctgctcca ggcatgcagt cgtctgggcg gtgctacaac tgggctggcg gcc         53

<210> SEQ ID NO 108
<211> LENGTH: 62
<212> TYPE: DNA
<213> ORGANISM: Homo sapiens

<400> SEQUENCE: 108
ggctgctcca ggcatgcaga tcccacaggc gtctgggcgg tgctacaact gggctggcgg   60
cc                                                                   62

<210> SEQ ID NO 109
<211> LENGTH: 74
<212> TYPE: DNA
<213> ORGANISM: Homo sapiens

<400> SEQUENCE: 109
ggctgctcca ggcatgcaga tcccacaggc gccctgccag tcgtctgggc ggtgctacaa   60
ctgggctggc ggcc                                                      74

<210> SEQ ID NO 110
<211> LENGTH: 59
<212> TYPE: DNA
<213> ORGANISM: Homo sapiens

<400> SEQUENCE: 110
ggctgctcca ggcatgcaga tccagtcgtc tgggcggtgc tacaactggg ctggcggcc    59
```

METHODS AND COMPOSITIONS FOR MODULATING PD1

CROSS-REFERENCE TO RELATED APPLICATIONS

The present application is a continuation of U.S. patent application Ser. No. 14/039,828, filed Sep. 27, 2013, which is a continuation of U.S. patent application Ser. No. 12/927,557, filed Nov. 17, 2010, now U.S. Pat. No. 8,563,314, which is a continuation-in-part of U.S. application Ser. No. 12/284,887, filed Sep. 25, 2008, which claims the benefit of U.S. Provisional Application No. 60/995,566, filed Sep. 27, 2007. U.S. patent application Ser. No. 12/927,557 claims the benefit of U.S. Provisional Application No. 61/281,432, filed Nov. 17, 2009. The disclosures of all the foregoing applications are hereby incorporated by reference in their entireties.

SEQUENCE LISTING

The instant application contains a Sequence Listing which has been submitted electronically in ASCII format and is hereby incorporated by reference in its entirety. Said ASCII copy, created on Jan. 27, 2016, is named 8325_0057_01 SEQLISTING.txt and is 22,691 bytes in size.

STATEMENT OF RIGHTS TO INVENTIONS MADE UNDER FEDERALLY SPONSORED RESEARCH

Not applicable.

TECHNICAL FIELD

The present disclosure is in the fields of genome engineering and nuclease identification.

BACKGROUND

Nucleases, including zinc finger nucleases and homing endonucleases such as ScelI, that are engineered to specifically bind to target sites have been shown to be useful in genome engineering. For example, zinc finger nucleases (ZFNs) are proteins comprising engineered site-specific zinc fingers fused to a nuclease domain. Such ZFNs have been successfully used for genome modification in a variety of different species. See, for example, United States Patent Publications 20030232410; 20050208489; 20050026157; 20050064474; 20060188987; 20060063231; and International Publication WO 07/014275, the disclosures of which are incorporated by reference in their entireties for all purposes. These ZFNs can be used to create a double-strand break (DSB) in a target nucleotide sequence, which increases the frequency of homologous recombination at the targeted locus more than 1000-fold. In addition, the inaccurate repair of a site-specific DSB by non-homologous end joining (NHEJ) can also result in gene disruption. Creation of two such DSBs results in deletion of arbitrarily large regions.

The programmed death receptor (PD1, also known as PDCD1) has been shown to be involved in regulating the balance between T cell activation and T cell tolerance in response to chronic antigens. During HIV1 infection, expression of PD1 has been found to be increased in CD4+ T cells. It is thought that PD1 up-regulation is somehow tied to T cell exhaustion (defined as a progressive loss of key effector functions) when T cell dysfunction is observed in the presence of chronic antigen exposure as is the case in HIV infection. PD1 up-regulation may also be associated with increased apoptosis in these same sets of cells during chronic viral infection (see Petrovas et al, (2009) *J Immunol.* 183(2):1120-32). PD1 may also play a role in tumor-specific escape from immune surveillance. It has been demonstrated that PD1 is highly expressed in tumor-specific cytotoxic T lymphocytes (CTLs) in both chronic myelogenous leukemia (CML) and acute myelogenous leukemia (AML). PD1 is also up-regulated in melanoma infiltrating T lymphocytes (TILs) (see Dotti (2009) *Blood* 114 (8): 1457-58). Tumors have been found to express the PD1 ligand (PDL) which, when combined with the up-regulation of PD1 in CTLs, may be a contributory factor in the loss in T cell functionality and the inability of CTLs to mediate an effective anti-tumor response. Researchers have shown that in mice chronically infected with lymphocytic choriomeningitis virus (LCMV), administration of anti-PD1 antibodies blocked PD1-PDL interaction and was able to restore some T cell functionality (proliferation and cytokine secretion), and lead to a decrease in viral load (Barber et al (2006) *Nature* 439(9): 682-687). Disregulation of PD1 may also play a role in autoimmune disease. SNPs of PD1 (in particular PD 1.3) have also been associated with increased risk for systemic lupus erythematosus (SLE). It has been shown that SLE patients have a higher frequency of the PD 1.3 PD1 allele, and that these patients show reduced PD1 expression on their activated CD4+ T cells (see Bertsias et al, (2009) *Arthritis Rheum.* 60(1):207-18).

Thus, there remains a need for additional PD1-targeted modulators, for example PD1-targeted nucleases or transcription factors that can be used in research and therapeutic applications.

SUMMARY

The present disclosure relates to development of PD1-targeted nucleases, for example engineered meganucleases and zinc finger nuclease (ZFNs).

The present disclosure demonstrates active zinc finger proteins specific for human and rodent PD1 and fusion proteins, including zinc finger protein transcription factors (ZFP-TFs) or zinc finger nucleases (ZFNs), comprising these PD1-specific zinc finger proteins. The proteins comprising PD1 specific zinc finger proteins of the invention may be used for research and therapeutic purposes, including for treatment of any disease or disorder in which PD1 is aberrantly expressed, or where the PD1 pathway is aberrantly utilized due to overexpression of a PD1 ligand. For example, zinc finger nuclease targeting of the PD1 locus in T cells can be used to block PD1-dependent immune suppression in both chronic infectious diseases and malignancies. Alternatively, a defective PD1 locus may be remedied using ZFN dependent targeted insertion of wild type sequences, or a zinc finger protein transcription factor (ZFP TF) may be used to modulate (e.g., upregulate or downregulate) defective PD1 expression. Further, a ZFP TF targeting the PD1 locus may be used to modulate a wild type PD1 gene.

In another aspect of the invention, the fusion proteins comprise zinc finger nucleases (ZFNs) that are specific for the human PD1 gene. In certain embodiments, the zinc finger domains of the nuclease fusion proteins comprise the non-naturally occurring recognition helices shown in Table 1 and/or bind to the target sites shown in Table 2.

In yet another aspect, provided herein are ZFP-TFs capable of modulating the expression of a PD1 gene. In certain embodiments, the zinc finger domains of the ZFP-TFs comprise the non-naturally occurring recognition helices shown in Tables 1 or 5 and/or bind to the target sites shown in Tables 2 or 6.

In another aspect, provided herein are methods and compositions for the regulation of the PD1 gene. In certain embodiments, the methods comprise introducing a fusion protein comprising a zinc finger protein that is engineered to bind to a target site in a PD1 gene (or polynucleotide encoding a fusion protein) into cells from a patient with a disease or disorder in which the disease or disorder is characterized by aberrant expression of PD1 and/or undesirable use of the PD1 pathway, caused by overexpression of the PD1 ligands. The methods may be utilized in the treatment and/or prevention of chronic infections such as HIV and HCV. Similarly, the methods and compositions may be utilized in the treatment and/or prevention of cancer and malignant disease. Non-limiting examples of cancers that can be treated and/or prevented include lung carcinomas, pancreatic cancers, liver cancers, bone cancers, breast cancers, colorectal cancers, leukemias, ovarian cancers, lymphomas, brain cancers and the like.

The methods and compositions described herein may be used as a stand-alone treatment, or may be used in combination with other anti-viral or anti-cancer therapies. These methods and compositions may be provided with anti-viral or anti-cancer therapies in a sequential fashion, or may be administered concurrently. The methods and compositions provided may also be used to modulate PD1 expression in a patient afflicted with an autoimmune disease, or may be used to treat such a patient by integrating in a wild type PD1 allele, or a PD1 allele with altered characteristics if this patient carried a defective or undesirable allele. Cell lines may be constructed to specifically alter that PD1 gene sequence to create screening systems for therapeutic compounds which may alter the regulation or functionality of a PD1 gene.

BRIEF DESCRIPTION OF THE DRAWINGS

FIG. 2 depicts the results of an analysis to determine the sequence (SEQ ID NO: 81) of the PD1 locus in CD8+ T cells following treatment with the PD1 specific ZFN pair 12942 and 12947 which target exon 1. Insertions are depicted in capitol letter in bold (SEQ ID NO 82-95). Deletions are denoted with a (–) (SEQ ID NOS 96-110). As can be seen from the figure, several insertions and deletions were observed near the ZFN cut site as a result of DSB repair via NHEJ.

FIG. 3 depicts the results following transfection of splenocytes derived from Pmel TCR transgenic/Rag1–/– mice with murine PD1-specific ZFNs. Cells were stimulated with anti-CD3 antibodies, and then stained for PD1. The plots show the percent PD1 positive CD3+CD8+ cells in each group and the median PD1 fluorescence for each group, and the data is represented in table format below. As can be seen in the figure, PD1 expression decreases in cells that received the PD1-specific ZFNs, even in the presence of CD3 stimulation.

FIG. 4 demonstrates that the reduction in PD1 expression was evident at later time points. Cells were also harvested at 72 hours post-CD3 stimulation, and stained for PD1. The upper histograms show the percent PD1 positive CD3+CD8+ cells in each group and the median PD1 fluorescence for each group. Lower plots show the frequency of PD1/CFSE expressing cells. This figure demonstrates that PD1 expression is still decreased in the cells treated with the PD1-specific ZFNs even 72 hours post CD3 stimulation.

FIG. 6 depicts the purification of PD1 (–) cells following treatment with the PD1 specific ZFN pairs into CD4+ T cells. Percent editing or NHEJ was measured by the Cel-I assay as described above, and up to 44% editing was observed with some of the PD1-specific ZFN pairs. Following treatment, the cells were stimulated with a first exposure to anti-CD3/CD8 beads to induce the ZFN transgenes and then re-stimulated and subjected to a purification procedure, either by FACs or by affinity chromatography. Cells were collected and analyzed for PD1 editing by the Cel-I assay (described above), i) following the first stimulation, ii) following the second stimulation but prior to any purification, iii) following cell sorting for CD25+ (a marker of activation), PD1(–), or iv) after affinity chromatography. As shown, using the cell sorting technique, up to 56% of the recovered cells were found to be modified. PD1(–) cells purified by the affinity chromatography displayed an overall PD1 modification of up to 42% as assayed by Cel-1 analysis.

FIG. 7 is a graph depicting results for PD1 specific ZFNs tested in CD8+ T cells. In this experiment, mRNAs encoding the PD1 specific ZFNs were transduced into CD8+ T and the percent PD1 modification was analyzed by the Cel I assay. The amount of modification observed was related to the amount of mRNA used, with lesser amounts of input mRNA resulting in lesser percentages of target modification. These results demonstrate that the PD1 specific ZFNs described herein are capable of modifying the PD1 locus in cell lines and in primary T cells.

DETAILED DESCRIPTION

Figure 1:
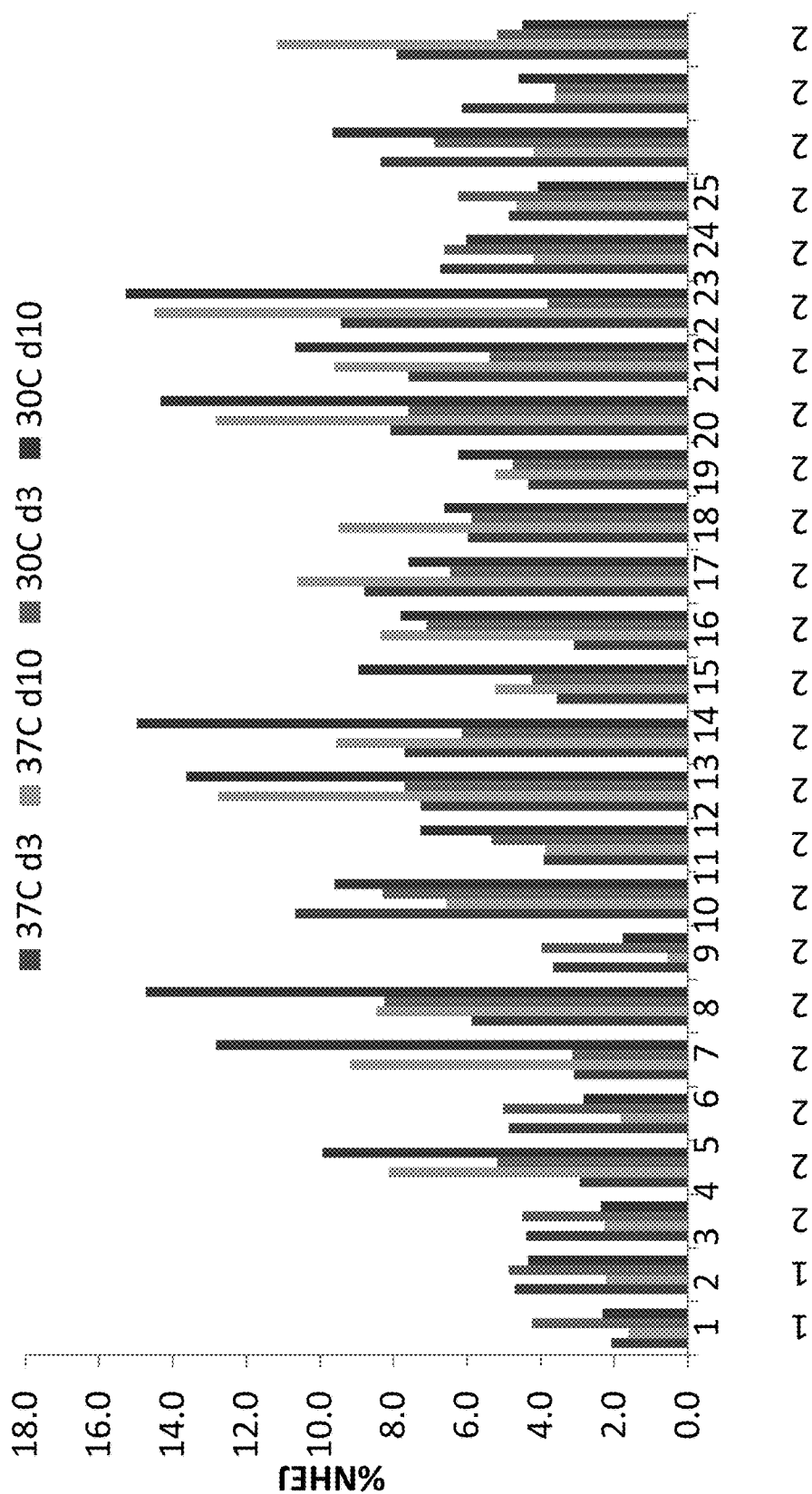
FIG. 1 is a graph showing the disruption of the PD1 gene in human PBMCs using PD1 specific zinc finger nucleases, as determined by the Cel-1 based SURVEYOR™ Nuclease assay which measures the percentage of mutations inserted by non-homologous end joining (NHEJ) that is induced when the indicated ZFNs are introduced into these cells. Cells were treated with ZFN pairs that each combined the ZFN 12942 with a different ZFN variant that bound on the opposite strand of DNA and would form a functional nuclease upon binding to the target locus with 12942. The SBS number for the second ZFN of the pair is indicated below each graph. The left-most bar of each pair shows NHEJ percentages three-days post nucleofection for cells incubated at 37° C. The bar second from the left on each indicated pair shows NHEJ percentages ten-days post nucleofection for cells incubated at 37° C. The bar second from the right on each indicated pair shows NHEJ percentages three-days post nucleofection for cells incubated at 30° C. and the right-most bar of each indicated pair shows NHEJ percentages ten-days post nucleofection for cells incubated at 30° C.

Described herein are compositions and methods for high throughput in vivo screening systems for identifying functional nucleases. In particular, the assays use a reporter system to monitor the ability of a nuclease to induce a double-stranded break at their target site. In addition, the assays can be used to determine the effect of the nuclease on cell growth (toxicity).

Engineered nuclease technology is based on the engineering of naturally occurring DNA-binding proteins. For example, engineering of homing endonucleases with tailored DNA-binding specificities has been described. Chames et al. (2005) *Nucleic Acids Res* 33(20):e178; Arnould et al. (2006) *J. Mol. Biol.* 355:443-458. In addition, engineering of ZFPs has also been described. See, e.g., U.S. Pat. Nos. 6,534,261; 6,607,882; 6,824,978; 6,979,539; 6,933,113; 7,163,824; and 7,013,219.

In addition, ZFPs have been attached to nuclease domains to create ZFNs—a functional entity that is able to recognize its intended gene target through its engineered (ZFP) DNA binding domain and the nuclease causes the gene to be cut near the ZFP binding site. See, e.g., Kim et al. (1996) *Proc Natl Acad Sci USA* 93(3):1156-1160. More recently, ZFNs have been used for genome modification in a variety of organisms. See, for example, United States Patent Publications 20030232410; 20050208489; 20050026157; 20050064474; 20060188987; 20060063231; and International Publication WO 07/014275.

Although the rules that allow engineering of ZFPs to bind to specific DNA sequences are well characterized and accurately identify specific ZFPs, these same ZFPs may not bind with equal affinity and/or specificity when incorporated into a ZFN. For example, it is likely that the chromosomal substrate can affect the precise dimerization of nuclease domains in living cells, consequently diminishing the cleavage potential, and that the precise chromatin architecture over a given genomic locus will differentially affect the ability of ZFNs to bind and cleave their intended target sequence. In addition, it is difficult if not impossible for in vitro assays to mimic the search parameters that a designed DNA binding domain is subjected to when presented with a cellular genome in chromatinized form. As a result, it is essential to test numerous variants in the relevant organism, or cell lineage, to identify a ZFN displaying the optimal characteristics for gene modification.

Furthermore, since every in vivo system has its own peculiarities, it is necessary to develop specific detection assays to determine ZFN action. Thus, unlike previously described in vivo screening methods which screen for homing endonucleases with binding specificity different from the naturally occurring homing endonuclease, the methods described herein provide a rapid and efficient way of ranking nucleases already known to bind to a particular target site by predicting their in vivo functionality as well as the toxicity of a nuclease to the host cell.

Thus, the methods and compositions described herein provide highly efficient and rapid methods for identifying nucleases that are biologically active in vivo. In addition to accurately predicting in vivo nucleases functionality, the assays described herein also can be used to determine nuclease toxicity, thereby allowing identification of the safest and most functionally active proteins.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

Zinc finger binding domains can be "engineered" to bind to a predetermined nucleotide sequence. Non-limiting examples of methods for engineering zinc finger proteins are design and selection. A designed zinc finger protein is a protein not occurring in nature whose design/composition results principally from rational criteria. Rational criteria for design include application of substitution rules and computerized algorithms for processing information in a database storing information of existing ZFP designs and binding data. See, for example, U.S. Pat. Nos. 6,140,081; 6,453,242;

and 6,534,261; see also WO 98/53058; WO 98/53059; WO 98/53060; WO 02/016536 and WO 03/016496.

A "selected" zinc finger protein is a protein not found in nature whose production results primarily from an empirical process such as phage display, interaction trap or hybrid selection. See e.g., U.S. Pat. No. 5,789,538; U.S. Pat. No. 5,925,523; U.S. Pat. No. 6,007,988; U.S. Pat. No. 6,013,453; U.S. Pat. No. 6,200,759; WO 95/19431; WO 96/06166; WO 98/53057; WO 98/54311; WO 00/27878; WO 01/60970 WO 01/88197 and WO 02/099084.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, also, U.S. patent application Ser. No. 10/912,932 and Ser. No. 11/304,981 and U.S. Provisional Application No. 60/808,486 (filed May 25, 2006), incorporated herein by reference in their entireties.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value there between or there above), preferably between about 100 and 1,000 nucleotides in length (or any integer there between), more preferably between about 200 and 500 nucleotides in length. "Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

A "target site" or "target sequence" is a nucleic acid sequence that defines a portion of a nucleic acid to which a binding molecule will bind, provided sufficient conditions for binding exist. For example, the sequence 5'-GAATTC-3' is a target site for the Eco RI restriction endonuclease.

A "chronic infectious disease" is a disease caused by an infectious agent wherein the infection has persisted. Such a disease may include hepatitis (A, B, or C), herpes virus (e.g., VZV, HSV-1, HSV-6, HSV-II, CMV, and EBV), and HIV/AIDS. Non-viral examples may include chronic fungal diseases such Aspergillosis, Candidiasis, Coccidioidomycosis, and diseases associated with *Cryptococcus* and *Histoplasmosis*. None limiting examples of chronic bacterial infectious agents may be *Chlamydia pneumoniae, Listeria monocytogenes*, and *Mycobacterium tuberculosis*. The term "cancer" refers to any disease in which there is an unrestrained proliferation of cells, either within an organ or body tissue. Thus, the term includes any type of cancer or malignancy, including, but not limited to, ovarian cancer, leukemia, lung cancer, colorectal/colon cancer, CNS cancer, melanoma, renal cell carcinoma, plasmacytoma/myeloma, prostate cancer, breast cancer, and the like. As used herein, the term "tumor" refers to an abnormal growth of cells or tissues of the malignant type, unless otherwise specifically indicated and does not include a benign type tissue. The term "inhibits or inhibiting" as used herein means reducing growth/replication.

The term "autoimmune disease" refers to any disease or disorder in which the subject mounts a destructive immune response against its own tissues. Autoimmune disorders can affect almost every organ system in the subject (e.g., human), including, but not limited to, diseases of the nervous, gastrointestinal, and endocrine systems, as well as skin and other connective tissues, eyes, blood and blood vessels. Examples of autoimmune diseases include, but are not limited to Hashimoto's thyroiditis, Systemic lupus erythematosus, Sjogren's syndrome, Graves' disease, Scleroderma, Rheumatoid arthritis, Multiple sclerosis, Myasthenia gravis and Diabetes.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP DNA-binding domain and a cleavage domain) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the expression level of a gene. Modulation of expression can include, but is not limited to, gene activation and gene repression. Modulation may also be complete, i.e. wherein gene expression is totally inactivated or is activated to wildtype levels or beyond; or it may be partial, wherein gene expression is partially reduced, or partially activated to some fraction of wildtype levels."Eukaryotic" cells include, but are not limited to, fungal cells (such as yeast), plant cells, animal cells, mammalian cells and human cells (e.g., T-cells).

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP DNA-binding domain is fused to a cleavage domain, the ZFP DNA-binding domain and the cleavage domain are in operative linkage if, in the fusion polypeptide, the ZFP DNA-binding domain portion is able to bind its target site and/or its binding site, while the cleavage domain is able to cleave DNA in the vicinity of the target site. Similarly, with respect to a fusion polypeptide in which a ZFP DNA-binding domain is fused to an activation or repression domain, the ZFP DNA-binding domain and the activation or repression domain are in operative linkage if, in the fusion polypeptide, the ZFP DNA-binding domain portion is able to bind its target site and/or its binding site, while the activation domain is able to upregulate gene expression or the repression domain is able to downregulate gene expression.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one ore more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) *Nature* 340:245-246; U.S. Pat. No. 5,585,245 and PCT WO 98/44350.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning, and expression vehicles, as well as integrating vectors.

A "reporter gene" or "reporter sequence" refers to any sequence that produces a protein product that is easily measured, preferably although not necessarily in a routine assay. Suitable reporter genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG, His, myc, Tap, HA or any detectable amino acid sequence. "Expression tags" include sequences that encode reporters that may be operably linked to a desired gene sequence in order to monitor expression of the gene of interest.

Overview

Described herein are zinc finger protein-transcription factors (ZFP-TFs) and/or nucleases (e.g., ZFNs) targeted to the PD1 gene as well as compositions comprising and methods of using these ZFP-TFs and/or nucleases for treatment of disease or disorders in which PD1 is aberrantly or undesirably expressed, or wherein the PD1 pathway is aberrantly or undesirably utilized due to overexpression of a PD 1 ligand, including, for example, treatment of chronic infectious diseases, cancers, and/or autoimmmune diseases. For treatment of a subject with a disease or disorder that is ameliorated by the modulation of PD1 expression, the ZFP-TFs and/or nucleases described herein can be introduced in vivo or ex vivo into cells (e.g., primary cells isolated from a patient afflicted with such a disease). Following ZFP-TF and/or ZFN treatment, the cells may be reintroduced into the patient for use as a medicament in the treatment of a chronic infectious disease or cancer. Similarly, stem cells may be used that have been treated with the PD1-specific ZFNs and/or ZFP-TFs. These cells can be infused into an afflicted patient for treatment of such a medical condition.

The compositions and methods described herein thus allow for the modulation of a PD1 gene. PD1 expression may be knocked out, knocked down, upregulated or downregulated using PD1-specific ZFP TFs or ZFNs, depending on the need. PD1 expression may be downregulated with ZFP-TFs or one or more PD1-specific ZFNs, for example in patients afflicted with chronic infectious diseases or cancers, and may be upregulated in patients, for example patients with autoimmune disease. The methods and compositions of the invention also provide therapeutics comprising a polynucleotide encoding the PD1-specific ZFP TFs and/or nucleases, wherein the polynucleotide is administered directly to the patient. Further, the invention provides methods and compositions wherein the polynucleotide encoding the ZFP TFs and/or nucleases may be incorporated into a vector such as a viral delivery vehicle for systemic administration as a therapeutic to an afflicted patient.

DNA-Binding Domains

Described herein are compositions comprising a DNA-binding domain that specifically binds to a target site in a PD1 gene. Any DNA-binding domain can be used in the compositions and methods disclosed herein, including but not limited to a zinc finger DNA-binding domain or a DNA-binding domain from a meganuclease.

In certain embodiments, the DNA binding domain comprises a zinc finger protein. Preferably, the zinc finger protein is non-naturally occurring in that it is engineered to bind to a target site of choice. See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416; U.S. Pat. Nos. 6,453,242; 6,534,261; 6,599,692; 6,503,717; 6,689,558; 7,030,215; 6,794,136; 7,067,317; 7,262,054; 7,070,934; 7,361,635; 7,253,273; and U.S. Patent Publication Nos. 2005/0064474; 2007/0218528; 2005/0267061, all incorporated herein by reference in their entireties.

An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in co-owned WO 02/077227.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein. In addition, enhancement of binding specificity for zinc finger binding domains has been described, for example, in co-owned WO 02/077227.

Selection of target sites; ZFPs and methods for design and construction of fusion proteins (and polynucleotides encoding same) are known to those of skill in the art and described in detail in U.S. Pat. Nos. 6,140,0815; 789,538; 6,453,242; 6,534,261; 5,925,523; 6,007,988; 6,013,453; 6,200,759; WO 95/19431; WO 96/06166; WO 98/53057; WO 98/54311; WO 00/27878; WO 01/60970 WO 01/88197; WO 02/099084; WO 98/53058; WO 98/53059; WO 98/53060; WO 02/016536 and WO 03/016496.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

Alternatively, the DNA-binding domain may be derived from a nuclease. For example, the recognition sequences of homing endonucleases and meganucleases such as I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII are known. See also U.S. Pat. No. 5,420,032; U.S. Pat. No. 6,833,252; Belfort et al. (1997) *Nucleic Acids Res.* 25:3379-3388; Dujon et al. (1989) *Gene* 82:115-118; Perler et al. (1994) Nucleic Acids Res. 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue. In addition, the DNA-binding specificity of homing endonucleases and meganucleases can be engineered to bind non-natural target sites. See, for example, Chevalier et al. (2002) *Molec. Cell* 10:895-905; Epinat et al. (2003) *Nucleic Acids Res.* 31:2952-2962; Ashworth et al. (2006) *Nature* 441:656-659; Paques et al. (2007) *Current Gene Therapy* 7:49-66; U.S. Patent Publication No. 20070117128.

In certain embodiments, the DNA binding domain is an engineered zinc finger protein that binds (in a sequence-specific manner) to a target site in a PD1 gene and modulates expression of PD1. The ZFPs can bind selectively to either a mutant PD1 allele or a wildtype PD1 sequence. PD1 target sites typically include at least one zinc finger but can include a plurality of zinc fingers (e.g., 2, 3, 4, 5, 6 or more fingers). Usually, the ZFPs include at least three fingers. Certain of the ZFPs include four, five or six fingers. The ZFPs that include three fingers typically recognize a target site that includes 9 or 10 nucleotides; ZFPs that include four fingers typically recognize a target site that includes 12 to 14 nucleotides; while ZFPs having six fingers can recognize target sites that include 18 to 21 nucleotides. The ZFPs can also be fusion proteins that include one or more regulatory domains, wherein these regulatory domains can be transcriptional activation or repression domains.

In some embodiments, the DNA binding domain is an engineered domain from a TAL effector derived from the plant pathogen Xanthomonas (see Boch et al, (2009) *Science* 29 Oct. 2009 (10.1126/science. 117881) and Moscou and Bogdanove, (2009) *Science* 29 Oct. 2009 (10.1126/science.1178817).

Fusion Proteins

Fusion proteins comprising DNA-binding proteins (e.g., ZFPs) as described herein and a heterologous regulatory (functional) domain (or functional fragment thereof) are also provided. Common domains include, e.g., transcription factor domains (activators, repressors, co-activators, co-repressors), silencers, oncogenes (e.g., myc, jun, fos, myb, max, mad, rel, ets, bel, myb, mos family members etc.); DNA repair enzymes and their associated factors and modifiers; DNA rearrangement enzymes and their associated factors and modifiers; chromatin associated proteins and their modifiers (e.g. kinases, acetylases and deacetylases); and DNA modifying enzymes (e.g., methyltransferases, topoisomerases, helicases, ligases, kinases, phosphatases, polymerases, endonucleases) and their associated factors and modifiers. U.S. Patent Application Publication Nos. 20050064474; 20060188987 and 2007/0218528 for details regarding fusions of DNA-binding domains and nuclease cleavage domains, incorporated by reference in their entireties herein.

Suitable domains for achieving activation include the HSV VP16 activation domain (see, e.g., Hagmann et al., *J. Virol.* 71, 5952-5962 (1997)) nuclear hormone receptors (see, e.g., Torchia et al., *Curr. Opin. Cell. Biol.* 10:373-383 (1998)); the p65 subunit of nuclear factor kappa B (Bitko & Barik, *J. Virol.* 72:5610-5618 (1998) and Doyle & Hunt, *Neuroreport* 8:2937-2942 (1997)); Liu et al., *Cancer Gene Ther.* 5:3-28 (1998)), or artificial chimeric functional domains such as VP64 (Beerli et al., (1998) *Proc. Natl. Acad. Sci. USA* 95:14623-33), and degron (Molinari et al., (1999) *EMBO J.* 18, 6439-6447). Additional exemplary activation domains include, Oct 1, Oct-2A, Sp1, AP-2, and CTF1 (Seipel et al., *EMBO J.* 11, 4961-4968 (1992) as well as p300, CBP, PCAF, SRC1 PvALF, AtHD2A and ERF-2. See, for example, Robyr et al. (2000) *Mol. Endocrinol.* 14:329-347; Collingwood et al. (1999) *J. Mol. Endocrinol.* 23:255-275; Leo et al. (2000) *Gene* 245:1-11; Manteuffel-Cymborowska (1999) *Acta Biochim. Pol.* 46:77-89; McKenna et al. (1999) *J. Steroid Biochem. Mol. Biol.* 69:3-12; Malik et al. (2000) *Trends Biochem. Sci.* 25:277-283; and Lemon et al. (1999) *Curr. Opin. Genet. Dev.* 9:499-504. Additional exemplary activation domains include, but are not limited to, OsGAI, HALF-1, C1, AP1, ARF-5, -6, -7, and -8, CPRF1, CPRF4, MYC-RP/GP, and TRAB1. See, for example, Ogawa et al. (2000) *Gene* 245:21-29; Okanami et al. (1996) *Genes Cells* 1:87-99; Goff et al. (1991) *Genes Dev.* 5:298-309; Cho et al. (1999) *Plant Mol. Biol.* 40:419-429; Ulmason et al. (1999) *Proc. Natl. Acad. Sci. USA* 96:5844-5849; Sprenger-Haussels et al. (2000) *Plant J.* 22:1-8; Gong et al. (1999) *Plant Mol. Biol.* 41:33-44; and Hobo et al. (1999) *Proc. Natl. Acad. Sci. USA* 96:15,348-15,353.

It will be clear to those of skill in the art that, in the formation of a fusion protein (or a nucleic acid encoding same) between a DNA-binding domain and a functional domain, either an activation domain or a molecule that interacts with an activation domain is suitable as a functional domain. Essentially any molecule capable of recruiting an activating complex and/or activating activity (such as, for example, histone acetylation) to the target gene is useful as an activating domain of a fusion protein. Insulator domains, localization domains, and chromatin remodeling proteins such as ISWI-containing domains and/or methyl binding domain proteins suitable for use as functional domains in fusion molecules are described, for example, in co-owned U.S. Patent Applications 2002/0115215 and 2003/0082552 and in co-owned WO 02/44376.

Exemplary repression domains include, but are not limited to, KRAB A/B, KOX, TGF-beta-inducible early gene (TIEG), v-erbA, SID, MBD2, MBD3, members of the DNMT family (e.g., DNMT1, DNMT3A, DNMT3B), Rb, and MeCP2. See, for example, Bird et al. (1999) *Cell* 99:451-454; Tyler et al. (1999) *Cell* 99:443-446; Knoepfler et al. (1999) *Cell* 99:447-450; and Robertson et al. (2000) *Nature Genet.* 25:338-342. Additional exemplary repression domains include, but are not limited to, ROM2 and AtHD2A. See, for example, Chem et al. (1996) *Plant Cell* 8:305-321; and Wu et al. (2000) *Plant J.* 22:19-27.

Fusion molecules are constructed by methods of cloning and biochemical conjugation that are well known to those of skill in the art. Fusion molecules comprise a DNA-binding domain and a functional domain (e.g., a transcriptional activation or repression domain). Fusion molecules also optionally comprise nuclear localization signals (such as, for example, that from the SV40 medium T-antigen) and epitope tags (such as, for example, FLAG and hemagglutinin). Fusion proteins (and nucleic acids encoding them) are designed such that the translational reading frame is preserved among the components of the fusion.

Fusions between a polypeptide component of a functional domain (or a functional fragment thereof) on the one hand, and a non-protein DNA-binding domain (e.g., antibiotic, intercalator, minor groove binder, nucleic acid) on the other, are constructed by methods of biochemical conjugation known to those of skill in the art. See, for example, the Pierce Chemical Company (Rockford, Ill.) Catalogue. Methods and compositions for making fusions between a minor groove binder and a polypeptide have been described. Mapp et al. (2000) *Proc. Natl. Acad. Sci. USA* 97:3930-3935.

In certain embodiments, the target site bound by the zinc finger protein is present in an accessible region of cellular chromatin. Accessible regions can be determined as described, for example, in co-owned International Publication WO 01/83732. If the target site is not present in an accessible region of cellular chromatin, one or more accessible regions can be generated as described in co-owned WO 01/83793. In additional embodiments, the DNA-binding domain of a fusion molecule is capable of binding to cellular chromatin regardless of whether its target site is in an accessible region or not. For example, such DNA-binding domains are capable of binding to linker DNA and/or nucleosomal DNA. Examples of this type of "pioneer" DNA binding domain are found in certain steroid receptor and in hepatocyte nuclear factor 3 (HNF3). Cordingley et al. (1987) *Cell* 48:261-270; Pina et al. (1990) *Cell* 60:719-731; and Cirillo et al. (1998) *EMBO J.* 17:244-254.

The fusion molecule may be formulated with a pharmaceutically acceptable carrier, as is known to those of skill in the art. See, for example, Remington's Pharmaceutical Sciences, 17th ed., 1985; and co-owned WO 00/42219.

The functional component/domain of a fusion molecule can be selected from any of a variety of different components capable of influencing transcription of a gene once the fusion molecule binds to a target sequence via its DNA binding domain. Hence, the functional component can include, but is not limited to, various transcription factor domains, such as activators, repressors, co-activators, co-repressors, and silencers.

Additional exemplary functional domains are disclosed, for example, in co-owned U.S. Pat. No. 6,534,261 and US Patent Application Publication No. 2002/0160940.

Functional domains that are regulated by exogenous small molecules or ligands may also be selected. For example, RheoSwitch® technology may be employed wherein a functional domain only assumes its active conformation in the presence of the external RheoChem™ ligand (see for example US 20090136465). Thus, the ZFP may be operably linked to the regulatable functional domain wherein the resultant activity of the ZFP-TF is controlled by the external ligand. In certain embodiments, the fusion protein comprises a DNA-binding binding domain and cleavage (nuclease) domain. As such, gene modification can be achieved using a nuclease, for example an engineered nuclease. Engineered nuclease technology is based on the engineering of naturally occurring DNA-binding proteins. The methods and compositions described herein are broadly applicable and may involve any nuclease of interest. Non-limiting examples of nucleases include meganucleases and zinc finger nucleases. The nuclease may comprise heterologous DNA-binding and cleavage domains (e.g., zinc finger nucleases; meganuclease DNA-binding domains with heterologous cleavage domains) or, alternatively, the DNA-binding domain of a naturally-occurring nuclease may be altered to bind to a selected target site (e.g., a meganuclease that has been engineered to bind to site different than the cognate binding site). For example, engineering of homing endonucleases with tailored DNA-binding specificities has been described, see Chames et al. (2005) *Nucleic Acids Res* 33(20):e178; Arnould et al. (2006) *J. Mol. Biol.* 355:443-458 and Grizot et al (2009) *Nucleic Acids Res* July 7 e publication. In addition, engineering of ZFPs has also been described. See, e.g., U.S. Pat. Nos. 6,534,261; 6,607,882; 6,824,978; 6,979,539; 6,933,113; 7,163,824; and 7,013,219.

In certain embodiment, the nuclease is a meganuclease (homing endonuclease). Naturally-occurring meganucleases recognize 15-40 base-pair cleavage sites and are commonly grouped into four families: the LAGLIDADG (SEQ ID NO: 79) family, the GIY-YIG family, the His-Cyst box family and the HNH family. Exemplary homing endonucleases include I-SceI, I-CeuI, PI-PspI, PI-Sce, I-SceIV, I-CsmI, I-PanI, I-SceII, I-PpoI, I-SceIII, I-CreI, TevI, I-TevII and I-TevIII. Their recognition sequences are known. See also U.S. Pat. No. 5,420,032; U.S. Pat. No. 6,833,252; Belfort et al. (1997) *Nucleic Acids Res.* 25:3379-3388; Dujon et al. (1989) *Gene* 82:115-118; Perler et al. (1994) *Nucleic Acids Res.* 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue.

DNA-binding domains from naturally-occurring meganucleases, primarily from the LAGLIDADG (SEQ ID NO: 79) family, have been used to promote site-specific genome modification in plants, yeast, *Drosophila*, mammalian cells and mice, but this approach has been limited to the modification of either homologous genes that conserve the meganuclease recognition sequence (Monet et al. (1999), *Biochem. Biophysics. Res. Common.* 255: 88-93) or to pre-engineered genomes into which a recognition sequence has been introduced (Route et al. (1994), *Mol. Cell. Biol.* 14: 8096-106; Chilton et al. (2003), *Plant Physiology.* 133: 956-65; Puchta et al. (1996), *Proc. Natl. Acad. Sci. USA* 93: 5055-60; Rong et al. (2002), *Genes Dev.* 16: 1568-81; Gouble et al. (2006), *J. Gene Med.* 8(5):616-622). Accordingly, attempts have been made to engineer meganucleases to exhibit novel binding specificity at medically or biotechnologically relevant sites (Porteus et al. (2005), *Nat. Biotechnol.* 23: 967-73; Sussman et al. (2004), *J. Mol. Biol.* 342: 31-41; Epinat et al. (2003), *Nucleic Acids Res.* 31: 2952-62; Chevalier et al. (2002) *Molec. Cell* 10:895-905; Epinat et al. (2003) *Nucleic Acids Res.* 31:2952-2962; Ashworth et al. (2006) *Nature* 441:656-659; Paques et al. (2007) *Current Gene Therapy* 7:49-66; U.S. Patent Publication Nos. 20070117128; 20060206949; 20060153826; 20060078552; and 20040002092). In addition, naturally-occurring or engineered DNA-binding domains from meganucleases have also been operably linked with a cleavage domain from a heterologous nuclease (e.g., FokI).

In other embodiments, the nuclease is a zinc finger nuclease (ZFN). ZFNs comprise a zinc finger protein that has been engineered to bind to a target site in a gene of choice and cleavage domain or a cleavage half-domain.

As noted above, zinc finger binding domains can be engineered to bind to a sequence of choice. See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416. An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in co-owned WO 02/077227.

Selection of target sites; ZFNs and methods for design and construction of fusion proteins (and polynucleotides encoding same) are known to those of skill in the art and described in detail in U.S. Patent Application Publication Nos. 20050064474 and 20060188987, incorporated by reference in their entireties herein.

In addition, as disclosed in these and other references, zinc finger domains and/or multi-fingered zinc finger proteins may be linked together using any suitable linker sequences, including for example, linkers of 5 or more amino acids in length. See, e.g., U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

Nucleases such as ZFNs and/or meganucleases also comprise a nuclease (cleavage domain, cleavage half-domain). As noted above, the cleavage domain may be heterologous to the DNA-binding domain, for example a zinc finger DNA-binding domain and a cleavage domain from a nuclease or a meganuclease DNA-binding domain and cleavage domain from a different nuclease. Heterologous cleavage domains can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Ma.; and Belfort et al. (1997) *Nucleic Acids Res.* 25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) Nucleases, Cold Spring Harbor Laboratory Press, 1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite et al. (1998) *Proc. Natl. Acad. Sci. USA* 95: 10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger-Fok I fusions, two fusion proteins, each comprising a FokI cleavage half-domain, can be used to reconstitute a catalytically active cleavage domain. Alternatively, a single polypeptide molecule containing a zinc finger binding domain and two Fok I cleavage half-domains can also be used. Parameters for targeted cleavage and targeted sequence alteration using zinc finger-Fok I fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in International Publication WO 07/014275, incorporated herein in its entirety. Additional restriction enzymes also contain separable binding and cleavage domains, and these are contemplated by the present disclosure. See, for example, Roberts et al. (2003) *Nucleic Acids Res.* 31:418-420.

In certain embodiments, the cleavage domain comprises one or more engineered cleavage half-domain (also referred to as dimerization domain mutants) that minimize or prevent homodimerization, as described, for example, in U.S. Patent Publication Nos. 20050064474 and 20060188987 and in U.S. application Ser. No. 11/805,850 (filed May 23, 2007), the disclosures of all of which are incorporated by reference in their entireties herein. Amino acid residues at positions 446, 447, 479, 483, 484, 486, 487, 490, 491, 496, 498, 499, 500, 531, 534, 537, and 538 of Fok I are all targets for influencing dimerization of the Fok I cleavage half-domains.

Exemplary engineered cleavage half-domains of Fok I that form obligate heterodimers include a pair in which a first cleavage half-domain includes mutations at amino acid residues at positions 490 and 538 of Fok I and a second cleavage half-domain includes mutations at amino acid residues 486 and 499.

Thus, in one embodiment, a mutation at 490 replaces Glu (E) with Lys (K); the mutation at 538 replaces Iso (I) with Lys (K); the mutation at 486 replaced Gln (Q) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E: I499L". The engineered cleavage half-domains described herein are obligate heterodimer mutants in which aberrant cleavage is minimized or abolished. See, e.g., Example 1 of U.S. Provisional Application No. 60/808,486 (filed May 25, 2006), the disclosure of which is incorporated by reference in its entirety for all purposes.

Engineered cleavage half-domains described herein can be prepared using any suitable method, for example, by site-directed mutagenesis of wild-type cleavage half-domains (Fok I) as described in Example 5 of U.S. Patent Publication No. 20050064474 and Example 38 of U.S. Patent Publication Nos. 2007/0305346 and 2008/0131962 and U.S. Patent Provisional Application Nos. 61/337,769, filed Feb. 8, 2010 and 61/403,916, filed Sep. 23, 2010.

Nuclease expression constructs can be readily designed using methods known in the art. See, e.g., United States Patent Publications 20030232410; 20050208489; 20050026157; 20050064474; 20060188987; 20060063231; and International Publication WO 07/014275. In certain embodiments, expression of the nuclease is under the control of an inducible promoter, for example the galactokinase promoter which is activated (de-repressed) in the presence of raffinose and/or galactose and repressed in presence of glucose. In particular, the galactokinase promoter is induced and the nuclease(s) expressed upon successive changes in the carbon source (e.g., from glucose to raffinose to galactose). Other non-limiting examples of inducible promoters include CUP1, MET15, PHO5, and tet-responsive promoters.

Delivery

The proteins (e.g., ZFPs), polynucleotides encoding same and compositions comprising the proteins and/or polynucleotides described herein may be delivered to a target cell by any suitable means. Suitable cells include but not limited to eukaryotic and prokaryotic cells and/or cell lines. Non-limiting examples of such cells or cell lines generated from such cells include COS, CHO (e.g., CHO-S, CHO-K1, CHO-DG44, CHO-DUXB11, CHO-DUKX, CHOK1SV), VERO, MDCK, WI38, V79, B14AF28-G3, BHK, HaK, NS0, SP2/0-Ag14, HeLa, HEK293 (e.g., HEK293-F, HEK293-H, HEK293-T), and perC6 cells as well as insect cells such as *Spodoptera fugiperda* (Sf), or fungal cells such as *Saccharomyces*, *Pichia* and *Schizosaccharomyces*. In certain embodiments, the cell line is a CHO-K1, MDCK or HEK293 cell line. Suitable primary cells include peripheral blood mononuclear cells (PBMC), and other blood cell subsets such as, but not limited to, CD4+ T cells or CD8+ T cells. Suitable cells also include stem cells such as, by way of example, embryonic stem cells, induced pluripotent stem cells, hematopoietic stem cells, neuronal stem cells and mesenchymal stem cells.

Methods of delivering proteins comprising zinc finger proteins as described herein are described, for example, in U.S. Pat. Nos. 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

Zinc finger proteins as described herein may also be delivered using vectors containing sequences encoding one or more of the zinc finger protein(s). Any vector systems may be used including, but not limited to, plasmid vectors, retroviral vectors, lentiviral vectors, adenovirus vectors, poxvirus vectors; herpesvirus vectors and adeno-associated virus vectors, etc. See, also, U.S. Pat. Nos. 6,534,261; 6,607,882; 6,824,978; 6,933,113; 6,979,539; 7,013,219; and 7,163,824, incorporated by reference herein in their entireties. Furthermore, it will be apparent that any of these vectors may comprise one or more zinc finger protein-encoding sequences. Thus, when one or more ZFPs are introduced into the cell, the ZFPs may be carried on the same vector or on different vectors. When multiple vectors are used, each vector may comprise a sequence encoding one or multiple ZFPs.

Conventional viral and non-viral based gene transfer methods can be used to introduce nucleic acids encoding engineered ZFPs in cells (e.g., mammalian cells) and target tissues. Such methods can also be used to administer nucleic acids encoding ZFPs to cells in vitro. In certain embodiments, nucleic acids encoding ZFPs are administered for in vivo or ex vivo gene therapy uses. Non-viral vector delivery systems include DNA plasmids, naked nucleic acid, and nucleic acid complexed with a delivery vehicle such as a liposome or poloxamer. Viral vector delivery systems include DNA and RNA viruses, which have either episomal or integrated genomes after delivery to the cell. For a review of gene therapy procedures, see Anderson, *Science* 256:808-813 (1992); Nabel & Felgner, *TIBTECH* 11:211-217 (1993); Mitani & Caskey, *TIBTECH* 11:162-166 (1993); Dillon, *TIBTECH* 11:167-175 (1993); Miller, *Nature* 357:455-460 (1992); Van Brunt, *Biotechnology* 6(10):1149-1154 (1988); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* Doerfler and Böhm (eds.) (1995); and Yu et al., *Gene Therapy* 1:13-26 (1994).

Methods of non-viral delivery of nucleic acids include electroporation, lipofection, microinjection, biolistics, virosomes, liposomes, immunoliposomes, polycation or lipid:nucleic acid conjugates, naked DNA, artificial virions, and agent-enhanced uptake of DNA. Sonoporation using, e.g., the Sonitron 2000 system (Rich-Mar) can also be used for delivery of nucleic acids.

Additional exemplary nucleic acid delivery systems include those provided by Amaxa® Biosystems (Cologne, Germany), Maxcyte, Inc. (Rockville, Md.), BTX Molecular Delivery Systems (Holliston, Ma.) and Copernicus Therapeutics Inc, (see for example U.S. Pat. No. 6,008,336). Lipofection is described in e.g., U.S. Pat. No. 5,049,386, U.S. Pat. No. 4,946,787; and U.S. Pat. No. 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiarmid et at (2009) *Nature Biotechnology* vol 27(7) p. 643).

The use of RNA or DNA viral based systems for the delivery of nucleic acids encoding engineered ZFPs take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of ZFPs include, but are not limited to, retroviral, lentivirus, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g., Buchscher et al., *J. Virol.* 66:2731-2739 (1992); Johann et al., *J. Virol.* 66:1635-1640 (1992); Sommerfelt et al., *Virol.* 176:58-59 (1990); Wilson et al., *J. Virol.* 63:2374-2378 (1989); Miller et al., *J. Virol.* 65:2220-2224 (1991); PCT/US94/05700).

In applications in which transient expression is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:38-47 (1987); U.S. Pat. No. 4,797,368; WO 93/24641; Kotin, *Human Gene Therapy* 5:793-801 (1994); Muzyczka, *J. Clin. Invest.* 94:1351 (1994). Construction of recombinant AAV vectors are described in a number of publications, including U.S. Pat. No. 5,173,414; Tratschin et al., *Mol. Cell. Biol.* 5:3251-3260 (1985); Tratschin, et al., *Mol. Cell. Biol.* 4:2072-2081 (1984); Hermonat & Muzyczka, *PNAS* 81:6466-6470 (1984); and Samulski et al., *J. Virol.* 63:03822-3828 (1989).

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al., *Blood* 85:3048-305 (1995); Kohn et al., *Nat. Med.* 1:1017-102 (1995); Malech et al., *PNAS* 94:22 12133-12138 (1997)). PA317/pLASN was the first therapeutic vector used in a gene therapy trial. (Blaese et al., *Science* 270:475-480 (1995)). Transduction efficiencies of 50% or greater have been observed for MFG-S packaged vectors. (Ellem et al., *Immunol Immunother* 44(1):10-20 (1997); Dranoff et al., *Hum. Gene Ther.* 1:111-2 (1997).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 by inverted terminal repeats flanking the transgene expression cassette. Efficient gene transfer and stable transgene delivery due to integration into the genomes of the transduced cell are key features for this vector system. (Wagner et al., *Lancet* 351:9117 1702-3 (1998), Kearns et al., *Gene Ther.* 9:748-55 (1996)). Other AAV serotypes, including AAV1, AAV3, AAV4, AAV5, AAV6 and AAV8, can also be used in accordance with the present invention.

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including nondividing, differentiated cells such as those found in liver, kidney and muscle. Conventional Ad vectors have a large carrying capacity. An example of the use of an Ad vector in a clinical trial involved polynucleotide therapy for antitumor immunization with intramuscular injection (Sterman et al., *Hum. Gene Ther.* 7:1083-9 (1998)). Additional examples of the use of adenovirus vectors for gene transfer in clinical trials include Rosenecker et al., *Infection* 24:1 5-10 (1996); Sterman et al., *Hum. Gene Ther.* 9:7 1083-1089 (1998); Welsh et al., *Hum. Gene Ther.* 2:205-18 (1995); Alvarez et al., *Hum. Gene Ther.* 5:597-613 (1997); Topf et al., *Gene Ther.* 5:507-513 (1998); Sterman et al., *Hum. Gene Ther.* 7:1083-1089 (1998).

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al., *Proc. Natl. Acad. Sci. USA* 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with a ZFP nucleic acid (gene or cDNA), and re-infused back into the subject organism (e.g., patient). Various cell types suitable for ex vivo transfection are well known to those of skill in the art (see, e.g., Freshney et al., *Culture of Animal Cells, A Manual of Basic Technique* (3rd ed. 1994)) and the references cited therein for a discussion of how to isolate and culture cells from patients).

Suitable cells include but not limited to eukaryotic and prokaryotic cells and/or cell lines. Non-limiting examples of such cells or cell lines generated from such cells include COS, CHO (e.g., CHO-S, CHO-K1, CHO-DG44, CHO-DUXB11, CHO-DUKX, CHOK1SV), VERO, MDCK, WI38, V79, B14AF28-G3, BHK, HaK, NS0, SP2/0-Ag14, HeLa, HEK293 (e.g., HEK293-F, HEK293-H, HEK293-T), and perC6 cells as well as insect cells such as *Spodoptera fugiperda* (Sf), or fungal cells such as *Saccharomyces, Pichia* and *Schizosaccharomyces*. In certain embodiments, the cell line is a CHO-K1, MDCK or HEK293 cell line. Additionally, primary cells may be isolated and used ex vivo for reintroduction into the subject to be treated following treatment with the ZFNs. Suitable primary cells include peripheral blood mononuclear cells (PBMC), and other blood cell subsets such as, but not limited to, CD4+ T cells or CD8+ T cells. Suitable cells also include stem cells such as, by way of example, embryonic stem cells, induced pluripotent stem cells, hematopoietic stem cells, neuronal stem cells and mesenchymal stem cells.

In one embodiment, stem cells are used in ex vivo procedures for cell transfection and gene therapy. The advantage to using stem cells is that they can be differentiated into other cell types in vitro, or can be introduced into a mammal (such as the donor of the cells) where they will engraft in the bone marrow. Methods for differentiating CD34+ cells in vitro into clinically important immune cell types using cytokines such a GM-CSF, IFN-γ and TNF-α are known (see Inaba et al., *J. Exp. Med.* 176:1693-1702 (1992)).

Stem cells are isolated for transduction and differentiation using known methods. For example, stem cells are isolated from bone marrow cells by panning the bone marrow cells with antibodies which bind unwanted cells, such as CD4+ and CD8+ (T cells), CD45+ (panB cells), GR-1 (granulocytes), and Tad (differentiated antigen presenting cells) (see Inaba et al., *J. Exp. Med.* 176:1693-1702 (1992)).

Stem cells that have been modified may also be used in some embodiments. For example, stem cells that have been made resistant to apoptosis may be used as therapeutic compositions where the stem cells also contain the ZFP TFs of the invention. Resistance to apoptosis may come about, for example, by knocking out BAX and/or BAK using BAX- or BAK-specific ZFNs (see, U.S. patent application Ser. No. 12/456,043) in the stem cells, or those that are disrupted in a caspase, again using caspase-6 specific ZFNs for example. These cells can be transfected with the ZFP TFs that are known to regulate mutant or wildtype PD1.

Vectors (e.g., retroviruses, adenoviruses, liposomes, etc.) containing therapeutic ZFP nucleic acids can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Methods for introduction of DNA into hematopoietic stem cells are disclosed, for example, in U.S. Pat. No. 5,928,638. Vectors useful for introduction of transgenes into hematopoietic stem cells, e.g., CD34+ cells, include adenovirus Type 35.

Vectors suitable for introduction of transgenes into immune cells (e.g., T-cells) include non-integrating lentivirus vectors. See, for example, Ory et al. (1996) *Proc. Natl. Acad. Sci. USA* 93:11382-11388; Dull et al. (1998) *J. Virol.* 72:8463-8471; Zuffery et al. (1998) *J. Virol.* 72:9873-9880; Follenzi et al. (2000) *Nature Genetics* 25:217-222.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., *Remington's Pharmaceutical Sciences,* 17th ed., 1989).

Applications

The disclosed compositions and methods can be used for any application in which it is desired to modulate the expression of one or more PD1 genes. In particular, these methods and compositions can be used where modulation of a PD1 allele is desired, including but not limited to, therapeutic and research applications. The methods and compositions may be used to treat chronic infectious diseases such as HIV/AIDS and HCV. In addition, the methods and compositions may be used to treat cancers such as melanoma, ovarian cancer, colorectal/colon cancer, renal cell carcinoma, plasmacytoma/myeloma, breast cancer and lung cancer.

Diseases and conditions which PD1 repressing ZFP TFs or ZFNs can be used as therapeutic agents include, but are not limited to, chronic infectious diseases and cancer. Diseases and conditions in which activating a PD1 gene may be useful as a therapeutic treatment include autoimmune diseases such as systemic lupus erythematosus (SLE). Polynucleotides encoding ZFP TFs or ZFNs may be used as therapeutics themselves, or may be incorporated into vectors for delivery.

Methods and compositions comprising ZFP-TFs that repress a PD1 allele, and/or PD1 specific ZFNs may also be used in conjunction with other therapeutics designed to treat a chronic infectious disease or cancer. These ZFPs or ZFNs (or polynucleotides encoding these ZFPs or ZFNs) may be administered concurrently (e.g., in the same pharmaceutical compositions) or may be administered sequentially in any order. Any type of cancer can be treated, including, but not limited to lung carcinomas, pancreatic cancers, liver cancers, bone cancers, breast cancers, colorectal cancers, ovarian cancers, leukemias, lymphomas, brain cancers and the like. Similarly, ZFP TFs designed to activate a PD1 allele may be used with other therapeutics designed to treat an autoimmune disease.

Methods and compositions for treatment also include cell compositions wherein a mutant copy of the PD1 allele within cells isolated from a patient have been modified to a wild-type PD1 allele using a PD1-specific ZFN. These ex vivo modified cells are then reintroduced into the patient. Additionally, methods and compositions comprising modified stem cells are also envisioned. For example, stem cell compositions wherein a mutant copy of the PD1 allele within the stem cells has been modified to a wildtype PD1 allele using a PD1-specific ZFN. In other embodiments, stem cell compositions are provided wherein a wild-type PD1 allele within the stem cells has been modified using PD1-specific ZFNs. These compositions may be used in conjunction with other therapeutics. These compositions may be administered concurrently (e.g., in the same pharmaceutical compositions) or may be administered sequentially in any order.

The methods and compositions of the invention are also useful for the design and implementation of in vitro and in vivo models, for example, animal models of chronic infection, cancer or autoimmunity, which allows for the study of these disorders and furthers discovery of useful therapeutics.

The following Examples relate to exemplary embodiments of the present disclosure in which the nuclease comprises a ZFN. It will be appreciated that this is for purposes of exemplification only and that other nucleases can be used, for instance homing endonucleases (meganuclases) with engineered DNA-binding domains and/or fusions of naturally occurring of engineered homing endonucleases (meganuclases) DNA-binding domains and heterologous cleavage domains.

EXAMPLES

Example 1: Identification of Persistently Biologically Active PD1-Specific ZFNs

ZFNs were assembled against the human PD1 gene and were tested by ELISA and CEL1 assays as described in Miller et al. (2007) *Nat. Biotechnol.* 25:778-785 and U.S. Patent Publication No. 20050064474 and International Patent Publication WO2005/014791

Specific examples of ZFPs are disclosed in Table 1. The first column in this table is an internal reference name (number) for a ZFP. Table 2 lists target binding sites on PD1. "F" refers to the finger and the number following "F" refers to which zinc finger (e.g., "F1" refers to finger 1).

TABLE 1

Human PD1-targeted zinc finger proteins

| SBS # | Design | | | | | |
|---|---|---|---|---|---|---|
| | F1 | F2 | F3 | F4 | F5 | F6 |
| 12942 | QSGHLSR (SEQ ID NO: 1) | RSDSLSV (SEQ ID NO: 2) | HNDSRKN (SEQ ID NO: 3) | RSDDLTR (SEQ ID NO: 4) | RSDHLTQ (SEQ ID NO: 5) | N/A |
| 12946 | RSAALSR (SEQ ID NO: 6) | RSDDLTR (SEQ ID NO: 4) | RSDHLTT (SEQ ID NO: 7) | DRSALSR (SEQ ID NO: 8) | DRSALAR (SEQ ID NO: 9) | N/A |
| 12947 | RSAALAR (SEQ ID NO: 10) | RSDDLSK (SEQ ID NO: 11) | RNDHRKN (SEQ ID NO: 12) | DRSALSR (SEQ ID NO: 8) | DRSALAR (SEQ ID NO: 9) | N/A |
| 12934 | RSDHLSE (SEQ ID NO: 13) | TSSDRTK (SEQ ID NO: 14) | RSDHLSE (SEQ ID NO: 13) | QSASRKN (SEQ ID NO: 15) | N/A | N/A |
| 12971 | RSDVLSE (SEQ ID NO: 16) | RSANLTR (SEQ ID NO: 17) | RSDHLSQ (SEQ ID NO: 18) | TSSNRKT (SEQ ID NO: 19) | DRSNLSR (SEQ ID NO: 20) | RSDALAR (SEQ ID NO: 21) |

TABLE 1-continued

Human PD1-targeted zinc finger proteins

| SBS # | Design | | | | | |
|---|---|---|---|---|---|---|
| | F1 | F2 | F3 | F4 | F5 | F6 |
| 12972 | DDWNLSQ (SEQ ID NO: 22) | RSANLTR (SEQ ID NO: 17) | RSDHLSQ (SEQ ID NO: 18) | TSSNRKT (SEQ ID NO: 19) | DRSNLSR (SEQ ID NO: 20) | RSDALAR (SEQ ID NO: 21) |
| 18759 | RSSALSR (SEQ ID NO: 23) | RPLALKH (SEQ ID NO: 24) | RNDHRKN (SEQ ID NO: 12) | TRPVLKR (SEQ ID NO: 25) | DRSALAR (SEQ ID NO: 9) | N/A |
| 22237 | QSGHLSR (SEQ ID NO: 1) | RSDSLSV (SEQ ID NO: 2) | HNDSRKN (SEQ ID NO: 3) | RANSLLR (SEQ ID NO: 26) | RSDHLTQ (SEQ ID NO: 5) | N/A |
| 25005 | RPSTLHR (SEQ ID NO: 27) | RSDELTR (SEQ ID NO: 28) | RNNNLRT (SEQ ID NO: 29) | TRPVLKR (SEQ ID NO: 25) | DRSALAR (SEQ ID NO: 9) | N/A |
| 25006 | RPSTLHR (SEQ ID NO: 27) | RSDELTR (SEQ ID NO: 28) | TNWHLRT (SEQ ID NO: 30) | TRPVLKR (SEQ ID NO: 25) | DRSALAR (SEQ ID NO: 9) | N/A |
| 25010 | RPSTLHR (SEQ ID NO: 27) | RSDELTR (SEQ ID NO: 28) | RTPHLTL (SEQ ID NO: 31) | TRPVLKR (SEQ ID NO: 25) | DRSALAR (SEQ ID NO: 9) | N/A |
| 25011 | RPSTLHR (SEQ ID NO: 27) | RSDELTR (SEQ ID NO: 28) | RSAQLAT (SEQ ID NO: 32) | TRPVLKR (SEQ ID NO: 25) | DRSALAR (SEQ ID NO: 9) | N/A |
| 25012 | RPSTLHR (SEQ ID NO: 27) | RSDELTR (SEQ ID NO: 28) | RCTHLYL (SEQ ID NO: 33) | TRPVLKR (SEQ ID NO: 25) | DRSALAR (SEQ ID NO: 9) | N/A |
| 25013 | RPSTLHR (SEQ ID NO: 27) | RSDELTR (SEQ ID NO: 28) | RPTQRYS (SEQ ID NO: 34) | TRPVLKR (SEQ ID NO: 25) | DRSALAR (SEQ ID NO: 9) | N/A |
| 25014 | RPSTLHR (SEQ ID NO: 27) | RSDELTR (SEQ ID NO: 28) | RANHREC (SEQ ID NO: 35) | TRPVLKR (SEQ ID NO: 25) | DRSALAR (SEQ ID NO: 9) | N/A |
| 25015 | RPSTLHR (SEQ ID NO: 27) | RSDELTR (SEQ ID NO: 28) | RANHREC (SEQ ID NO: 35) | TRPVLKR (SEQ ID NO: 25) | DRSALAR (SEQ ID NO: 9) | N/A |
| 25016 | RKFARPS (SEQ ID NO: 36) | RNFSRSD (SEQ ID NO: 37) | HPHHRMC (SEQ ID NO: 38) | TRPVLKR (SEQ ID NO: 25) | DRSALAR (SEQ ID NO: 9) | N/A |
| 25017 | RPSTLHR (SEQ ID NO: 27) | RSDELTR (SEQ ID NO: 28) | RMGRLST (SEQ ID NO: 39) | TRPVLKR (SEQ ID NO: 25) | DRSALAR (SEQ ID NO: 9) | N/A |
| 25022 | RPSTLHR (SEQ ID NO: 27) | RSDELTR (SEQ ID NO: 28) | RHSRLTT (SEQ ID NO: 40) | TRPVLMR (SEQ ID NO: 41) | DRSALAR (SEQ ID NO: 9) | N/A |
| 25023 | RPSTLHR (SEQ ID NO: 27) | RSDELTR (SEQ ID NO: 28) | RANHRVC (SEQ ID NO: 42) | TRPVLKR (SEQ ID NO: 25) | DRSALAR (SEQ ID NO: 9) | N/A |
| 25025 | RPSTLHR (SEQ ID NO: 27) | RSDELTR (SEQ ID NO: 28) | RSTHLLG (SEQ ID NO: 43) | TRPVLKR (SEQ ID NO: 25) | DRSALAR (SEQ ID NO: 9) | N/A |
| 25027 | RNAALTR (SEQ ID NO: 45) | RSDELTR (SEQ ID NO: 28) | RSCGLWS (SEQ ID NO: 44) | TRPVLKR (SEQ ID NO: 25) | DRSALAR (SEQ ID NO: 9) | N/A |
| 25028 | CNAALTR (SEQ ID NO: 46) | RSDELTR (SEQ ID NO: 28) | REEHRAT (SEQ ID NO: 47) | TRPVLKR (SEQ ID NO: 25) | DRSALAR (SEQ ID NO: 9) | N/A |

TABLE 1-continued

Human PD1-targeted zinc finger proteins

| SBS # | Design | | | | | |
|---|---|---|---|---|---|---|
| | F1 | F2 | F3 | F4 | F5 | F6 |
| 25029 | RNAALTR (SEQ ID NO: 45) | RSDELTR (SEQ ID NO: 28) | RHHHLAA (SEQ ID NO: 48) | TRPVLKR (SEQ ID NO: 25) | DRSALAR (SEQ ID NO: 9) | N/A |
| 25030 | RNAALTR (SEQ ID NO: 45) | RSDELTR (SEQ ID NO: 28) | RPMHLTN (SEQ ID NO: 49) | TRPVLKR (SEQ ID NO: 25) | DRSALAR (SEQ ID NO: 9) | N/A |
| 25031 | RNAALTR (SEQ ID NO: 45) | RSDELTR (SEQ ID NO: 28) | RSPHLYH (SEQ ID NO: 50) | TRPVLKR (SEQ ID NO: 25) | DRSALAR (SEQ ID NO: 9) | N/A |
| 25032 | RNAALTR (SEQ ID NO: 45) | RSDELTR (SEQ ID NO: 28) | RCEALHH (SEQ ID NO: 51) | TRPVLKR (SEQ ID NO: 25) | DRSAQAR (SEQ ID NO: 52) | N/A |
| 25034 | RNAALTR (SEQ ID NO: 45) | RSDELTR (SEQ ID NO: 28) | RCEALHH (SEQ ID NO: 51) | TRPVLKR (SEQ ID NO: 25) | DRSALAR (SEQ ID NO: 9) | N/A |
| 25036 | RNAALTR (SEQ ID NO: 45) | RSDELTR (SEQ ID NO: 28) | RSPHLYH (SEQ ID NO: 50) | TRPVLKR (SEQ ID NO: 25) | DRSALAR (SEQ ID NO: 9) | N/A |
| 25040 | RNAALTR (SEQ ID NO: 45) | RSDELTR (SEQ ID NO: 28) | RLPALLS (SEQ ID NO: 53) | TRPVLKR (SEQ ID NO: 25) | DRSALAR (SEQ ID NO: 9) | N/A |
| 25041 | HNAALTR (SEQ ID NO: 54) | RSDELTR (SEQ ID NO: 28) | RTYNRTQ (SEQ ID NO: 55) | TRPVLKR (SEQ ID NO: 25) | DRSALAR (SEQ ID NO: 9) | N/A |

TABLE 2

ZFN Target sites in the human PD1gene

| SBS# | Target site |
|---|---|
| 12942 | ccAGGGCGCCTGTGGGAtctgcatgcct (SEQ ID NO: 56) |
| 12946 | caGTCGTCTGGGCGGTGctacaactggg (SEQ ID NO: 57) |
| 12947 | caGTCGTCTGGGCGGTGctacaactggg (SEQ ID NO: 57) |
| 12934 | gaACACAGGCACGGctgaggggtcctcc (SEQ ID NO: 58) |
| 12971 | ctGTGGACTATGGGGAGCTGgatttcca (SEQ ID NO: 59) |
| 12972 | ctGTGGACTATGGGGAGCTGgatttcca (SEQ ID NO: 59) |
| 18759 | caGTCGTCTGGGCGGTGct (SEQ ID NO: 60) |
| 22237 | ccAGGGCGCCTGTGGGAtctgcatgcct (SEQ ID NO: 56) |
| 25005 | caGTCGTCTGGGCGGTGct (SEQ ID NO: 60) |
| 25006 | caGTCGTCTGGGCGGTGct (SEQ ID NO: 60) |
| 25010 | caGTCGTCTGGGCGGTGct (SEQ ID NO: 60) |
| 25011 | caGTCGTCTGGGCGGTGct (SEQ ID NO: 60) |
| 25012 | caGTCGTCTGGGCGGTGct (SEQ ID NO: 60) |
| 25013 | caGTCGTCTGGGCGGTGct (SEQ ID NO: 60) |
| 25014 | caGTCGTCTGGGCGGTGct (SEQ ID NO: 60) |
| 25015 | caGTCGTCTGGGCGGTGct (SEQ ID NO: 60) |
| 25016 | caGTCGTCTGGGCGGTGct (SEQ ID NO: 60) |
| 25017 | caGTCGTCTGGGCGGTGct (SEQ ID NO: 60) |
| 25022 | caGTCGTCTGGGCGGTGct (SEQ ID NO: 60) |
| 25023 | caGTCGTCTGGGCGGTGct (SEQ ID NO: 60) |
| 25025 | caGTCGTCTGGGCGGTGct (SEQ ID NO: 60) |
| 25027 | caGTCGTCTGGGCGGTGct (SEQ ID NO: 60) |
| 25028 | caGTCGTCTGGGCGGTGct (SEQ ID NO: 60) |
| 25029 | caGTCGTCTGGGCGGTGct (SEQ ID NO: 60) |
| 25030 | caGTCGTCTGGGCGGTGct (SEQ ID NO: 60) |
| 25031 | caGTCGTCTGGGCGGTGct (SEQ ID NO: 60) |
| 25032 | caGTCGTCTGGGCGGTGct (SEQ ID NO: 60) |
| 25034 | caGTCGTCTGGGCGGTGct (SEQ ID NO: 60) |
| 25036 | caGTCGTCTGGGCGGTGct (SEQ ID NO: 60) |
| 25040 | caGTCGTCTGGGCGGTGct (SEQ ID NO: 60) |
| 25041 | caGTCGTCTGGGCGGTGct (SEQ ID NO: 60) |

Initial in vitro activity assays were performed on nucleofected cell samples as described (above. Briefly, the plasmid encoding ZFP-FokI fusions were introduced into K562 cells by transfection using the Amaxa™ Nucleofection kit as specified by the manufacturer. For transfection, two million K562 cells were mixed with varying amounts of each zinc-finger nuclease expression plasmid and 100 μL Amaxa™ Solution V. Cells were transfected in an Amaxa Nucleofector II™ using program T-16. Immediately following transfection, the cells were divided into two different flasks and grown in RPMI medium (Invitrogen) supplemented with 10% FBS in 5% $CO_2$ at either 30° C. or 37° C. for four days.

From this initial in vitro screen, two lead ZFN pairs were identified and submitted for elaboration in order to try to improve their efficiency. These pairs target exons 1 and 5 of the PD1 gene, respectively. The elaborated (improved) proteins were retested in a time-course experiment, essentially as described above. The results are summarized in Table 3 below.

TABLE 3

PD1 NHEJ

| Target | ZFN pair | % NHEJ | | |
|---|---|---|---|---|
| | | Day 3 | Day 7 | Day 9 |
| exon 1 | 12942/12946 | 8 | 7 | 5 |
| exon 1 | 12942/12947 | 10 | 6 | 6 |
| exon 5 | 12934/12971 | 11 | 6 | 1.5 |
| exon 5 | 12934/12972 | 11 | 7.5 | 2 |

As shown in Table 3, treatment of cells with ZFNs against exon 5 causes the loss of a greater proportion of genome-edited cells from the population, while the genome-editing signal in cells treated with ZFNs designed against exon 1 is much more stable.

To determine the ZFN activity at the PD1 locus, Cel-1 based SURVEYOR™ Nuclease assays were performed essentially as per the manufacturer's instructions (Trangenomic SURVEYOR™). Cells were harvested and chromosomal DNA prepared using a Quickextract™ Kit according to manufacturer's directions (Epicentre®). The appropriate region of the PD1 locus was PCR amplified using Accuprime™ High-fidelity DNA polymerase (Invitrogen). PCR reactions were heated to 94° C., and gradually cooled to room temperature. Approximately 200 ng of the annealed DNA was mixed with 0.33 μL Cel-I enzyme and incubated for 20 minutes at 42° C. Reaction products were analyzed by polyacrylamide gel electrophoresis in 1× Tris-borate-EDTA buffer.

Constructs were also tested in primary PBMC samples that had been held at either 30° C. or 37° C. for either 3 or 10 days (see Table 4). Briefly, PBMC were obtained from AllCells and were cultured in RPMI+10% FBS+1% L-Glutamine (30 mg/mL)+IL-2 (1 ng/mL, Sigma) and activated with anti-CD3/CD28 beads according to the manufacturer's protocol (Dynal). Cells were seeded at 3E5 cell/mL in 1 mL volume in a 24 well plate.

Adenoviral vectors were constructed containing the ZFN pairs of interest as described (see US Patent Publication 20080159996) and were added two days later at an MOI of 10, 30, or 100 (MOI calculated based on infectious titer).

Cells were harvested 3 or 10 days after exposure to virus and gene modification efficiency was determined using a Cel-I based SURVEYOR™ Nuclease assay, performed as described in International Patent Publication WO 07/014275. See, also, Oleykowski et al. (1998) *Nucleic Acids res.* 26:4597-4602; Qui et al. (2004) *BioTechniques* 36:702-707; Yeung et al. (2005) *BioTechniques* 38:749-758.

For the ZFN pairs shown in Table 4, each ZFN was tested in combination with ZFN 12942. Activity is measured by percent NHEJ activity as measured by the Cel-1 based SURVEYOR™ Nuclease assay described above.

Additional pairs of PD1 specific ZFNs were also tested for activity in primary PBMC as described above, and the results are shown in Table 4. In the data shown in Table 4, the PD1-specific monomer 12942 was always paired with the second ZFN listed in Table 4 to form an active pair (i.e. ZFN 12942 was paired with each of ZFN 12947 through 25041). See, also, FIG. 1 (samples are as indicated in Table 4).

TABLE 4

Activity of PD1 ZFNs

| 12942+ | 37° C. Day 3 (Percent NHEJ) | 37° C. Day 10 (Percent NHEJ) | 30° C. Day 3 (Percent NHEJ) | 30° C. Day 10 (Percent NHEJ) | Sample in FIG. 1 |
|---|---|---|---|---|---|
| 12947 | 2.1 | 1.6 | 4.2 | 2.3 | 1 |
| 18759 | 4.7 | 2.2 | 4.9 | 4.3 | 2 |
| 25005 | 4.4 | 2.3 | 4.5 | 2.4 | 3 |
| 25006 | 2.9 | 8.1 | 5.2 | 9.9 | 4 |
| 25010 | 4.9 | 1.8 | 5.0 | 2.8 | 5 |
| 25011 | 3.1 | 9.2 | 3.1 | 12.8 | 6 |
| 25012 | 5.9 | 8.5 | 8.2 | 14.7 | 7 |
| 25013 | 3.7 | 0.6 | 4.0 | 1.8 | 8 |
| 25014 | 10.7 | 6.6 | 8.3 | 9.6 | 9 |
| 25015 | 3.9 | 3.9 | 5.3 | 7.3 | 10 |
| 25016 | 7.3 | 12.8 | 7.7 | 13.6 | 11 |
| 25017 | 7.7 | 9.6 | 6.1 | 15.0 | 12 |
| 25022 | 3.6 | 5.2 | 4.2 | 9.0 | 13 |
| 25023 | 3.1 | 8.3 | 7.1 | 7.8 | 14 |
| 25025 | 8.8 | 10.6 | 6.5 | 7.6 | 15 |
| 25027 | 6.0 | 9.5 | 5.9 | 6.6 | 16 |
| 25028 | 4.3 | 5.2 | 4.8 | 6.2 | 17 |
| 25029 | 8.1 | 12.8 | 7.6 | 14.3 | 18 |
| 25030 | 7.6 | 9.6 | 5.4 | 10.7 | 19 |
| 25031 | 9.4 | 14.5 | 3.8 | 15.3 | 20 |
| 25032 | 6.7 | 4.2 | 6.6 | 6.0 | 21 |
| 25034 | 4.9 | 4.7 | 6.2 | 4.1 | 22 |
| 25036 | 8.3 | 4.2 | 6.9 | 9.7 | 23 |
| 25040 | 6.1 | 3.6 | 3.6 | 4.6 | 24 |
| 25041 | 7.9 | 11.2 | 5.2 | 4.5 | 25 |

To assay the local effects of the ZFN driven NHEJ activity at the molecular level, CD8+ cells were treated with the exon1 specific ZFN pair 12942 and 12947. Briefly, CD8+ cells were purchased from AllCells and were cultured in RPMI+10% FBS+1% L-Glutamine (30 mg/mL)+IL-2 (30 μg/mL, Sigma) and allowed to rest for 4-24 hours.

Plasmids were constructed containing the ZFN pairs of interest as described above and 1e6 cells/nucleofection were used with the Amaxa™ Nucleofection kit as specified by the manufacturer. Cells were activated 12-24 hours post nucleofection with anti-CD3/CD28 beads according to the manufacturer's protocol (Dynal).

Cells were harvested 3 or 10 days after nucleofection and gene modification efficiency was determined using a Cel-1 based SURVEYOR™ Nuclease assay, performed as described in International Patent Publication WO 07/014275. See, also, Oleykowski et al. (1998) *Nucleic Acids res.* 26:4597-4602; Qui et al. (2004) *BioTechniques* 36:702-707; Yeung et al. (2005) *BioTechniques* 38:749-758.

PCR products were cloned and transfected into *E. coli*. Antibiotic resistant subclones were grown up, the plasmids isolated and then subjected to sequence analysis to observe any sequence alterations that had occurred as a result of NHEJ (see FIG. 2). As can be seen from the figure, a variety of insertions and deletions were observed in the vicinity of the ZFN cleavage site.

These ZFNs were also tested in the yeast system as described in US Publication No. 20090111119.

Example 2: Ex Vivo Activity of PD1-Specific ZFNs in Mice

To test the concept of deleting PD1 in vivo, mouse PD1-specific ZFNs were made as described above and then tested ex vivo. The sequence characteristics of the zinc finger domains, as well as their binding specificities are shown below in Tables 5 and 6.

TABLE 5

Murine PD1-specific zinc finger designs

| SBS # | F1 | F2 | F3 | F4 | F5 | F6 |
|---|---|---|---|---|---|---|
| 14534 | DDWNLSQ (SEQ ID NO: 22) | RSANLTR (SEQ ID NO: 17) | TSGSLSR (SEQ ID NO: 61) | QSGDLTR (SEQ ID NO: 62) | QSSDLRR (SEQ ID NO: 63) | N/A |
| 14534-FokI KK | DDWNLSQ (SEQ ID NO: 22) | RSANLTR (SEQ ID NO: 17) | TSGSLSR (SEQ ID NO: 61) | QSGDLTR (SEQ ID NO: 62) | QSSDLRR (SEQ ID NO: 63) | N/A |
| 14536 | QSSHLTR (SEQ ID NO: 64) | RSDNLRE (SEQ ID NO: 65) | DRSNLSR (SEQ ID NO: 20) | TSSNRKT (SEQ ID NO: 19) | RSDSLSK (SEQ ID NO: 66) | QSANRTT (SEQ ID NO: 80) |
| 14536-FokI EL | QSSHLTR (SEQ ID NO: 64) | RSDNLRE (SEQ ID NO: 65) | DRSNLSR (SEQ ID NO: 20) | TSSNRKT (SEQ ID NO: 19) | RSDSLSK (SEQ ID NO: 66) | QSANRTT (SEQ ID NO: 80) |
| 14545 | QSGDLTR (SEQ ID NO: 62) | RSDNLSE (SEQ ID NO: 67) | ERANRNS (SEQ ID NO: 68) | DRSDLSR (SEQ ID NO: 69) | QSSDLRR (SEQ ID NO: 63) | N/A |
| 14545-FokI KK | QSGDLTR (SEQ ID NO: 62) | RSDNLSE (SEQ ID NO: 67) | ERANRNS (SEQ ID NO: 68) | DRSDLSR (SEQ ID NO: 69) | QSSDLRR (SEQ ID NO: 63) | N/A |
| 14546 | DRSHLAR (SEQ ID NO: 70) | RSDDLSR (SEQ ID NO: 71) | QSANRTK (SEQ ID NO: 72) | RSDTLSE (SEQ ID NO: 73) | ANSNRIK (SEQ ID NO: 74) | N/A |
| 14546-FokI EL | DRSHLAR (SEQ ID NO: 70) | RSDDLSR (SEQ ID NO: 71) | QSANRTK (SEQ ID NO: 72) | RSDTLSE (SEQ ID NO: 73) | ANSNRIK (SEQ ID NO: 74) | N/A |

TABLE 6

Binding specificities for Murine PD1-specific zinc finger designs

| SBS # | Target site |
|---|---|
| 14534 | gtGCTGCAGTTGAGCTGgcaatcagggt (SEQ ID NO: 75) |
| 14534-FokI KK | gtGCTGCAGTTGAGCTGgcaatcagggt (SEQ ID NO: 75) |
| 14536 | ccCAAGTGAATGACCAGGGTacctgccg (SEQ ID NO: 76) |
| 14536-FokI EL | ccCAAGTGAATGACCAGGGTacctgccg (SEQ ID NO: 76) |
| 14545 | caGCTGCCCAACAGGCAtgacttccaca (SEQ ID NO: 77) |
| 14545-FokI KK | caGCTGCCCAACAGGCAtgacttccaca (SEQ ID NO: 77) |
| 14546 | atGATCTGGAAGCGGGCatcctggacgg (SEQ ID NO: 78) |
| 14546-FokI EL | atGATCTGGAAGCGGGCatcctggacgg (SEQ ID NO: 78) |

On day 1, splenocytes harvested from Pmel TCR transgenic/Rag1−/− mice were processed into a single cell suspension and resuspended in complete media (RPMI-1640, 10% Fetal Bovine Serum, 0.1 mM nonessential amino acids, 1 mM sodium pyruvate, 2 mM L-glutamine, 50 µg/ml gentamicin sulfate, 50 µM 2-mercaptoethanol) with 25 µl of Invitrogen Mouse T-Activator CD3/CD28 Dynabeads/$10^6$ cells. Cells were plated in 24 well plate at $2\times10^6$ cells/ml (2 ml/well). On day 3, cells were harvested, separated from beads using a magnet and counted. Transfection of splenocytes was performed following the protocol provided with the Amaxa™ Nucleofection kit. Briefly, $1\times10e^7$ viable cells were resuspended in 100 µl of Amaxa Nucleofector Solution and transfected either with 4 µg of plasmid containing ZFN pair 14546 and 14545, or 4 µg of mut PD1 Fok1 plasmid containing ZFN pair 14546-FokI EL and 14545-Fok I KK, 2.5 µg of Amaxa pmax GFP vector, or a no DNA control, using Amaxa Nucleofector (program X-01). Cells were cultured in 2 ml of fully supplemented Amaxa Mouse T Cell Nucleofector Medium at 30° C. after transfection. The next day, one ml of Amaxa Mouse T cell Nucleofector Medium was removed and replaced with one ml of complete media supplemented with 10 U/ml IL-2. Two days later, cells were harvested and counted. Two million cells from the each of the groups were plated in anti-CD3 coated wells on a 24 well plate. The next day, cells were harvested and stained with anti-PD1 PE; anti-CD3 PE-Cy7, and anti-CD8 APC. Cells were analyzed on a BD FACSCalibur. Plots show % PD1 positive CD3+CD8+ cells in each group and the median PD1 fluorescence for each group (see FIG. 3). The data shows that PD1 expression is decreased in the cells that received the PD1-specific ZFNs, even in the presence of anti-CD3 stimulation.

To verify that the reduction in PD1 expression was evident at later time points, cells were also harvested at 72 hours post anti-CD3 stimulation, rather than at 24 hours as described above. Cells were harvested and stained with anti-PD1 PE; anti-CD3 PE-Cy7, and anti-CD8 APC. Cells were analyzed on a BD FACSCalibur. The data is presented in FIG. 4. The upper histograms show % PD1 positive CD3+CD8+ cells in each group and the median PD1 fluorescence for each group. Lower plots show the frequency of PD1/CF SE expressing cells. Importantly, mut PD1 Fok1 and wt PD1 Fok1 show higher frequency of PD1$^{neg}$ CFSE$^{dim}$ (dividing cells) than control groups, and demonstrate that PD1 expression is still decreased in the cells treated with the PD1-specific ZFNs even 72 hours post anti-CD3 stimulation.

Example 3: Activity of Human PD1-Specific ZFNs in TILs

Human PD1-specific ZFNs were tested in human tumor infiltrating lymphocytes (TILs) in the presence of tumors and assayed essentially as described above and using methods known in the art (see for example Yoshino et al, (1992) Cancer Research 52: 775-781). PD1-specific ZFNs were activated using anti-CD3 antibodies as described above, then the cells were transduced with Ad5/F35 adenovirus expressing PD1-specific ZFNs. Cells were expanded with IL2 and then restimulated with anti-CD3 antibodies or with tumors and assayed 24 hours post stimulation. The results are shown in Table 7 below.

ZFN mediated decrease in PD1 leads to an increase in TIL viability. Also, the data shows that a decrease in PD1 expression in the transduced TILs leads to a decrease in tumor cell viability.

Example 4: Purification of PD1 Edited Primary Human T Cells

Figure 5:
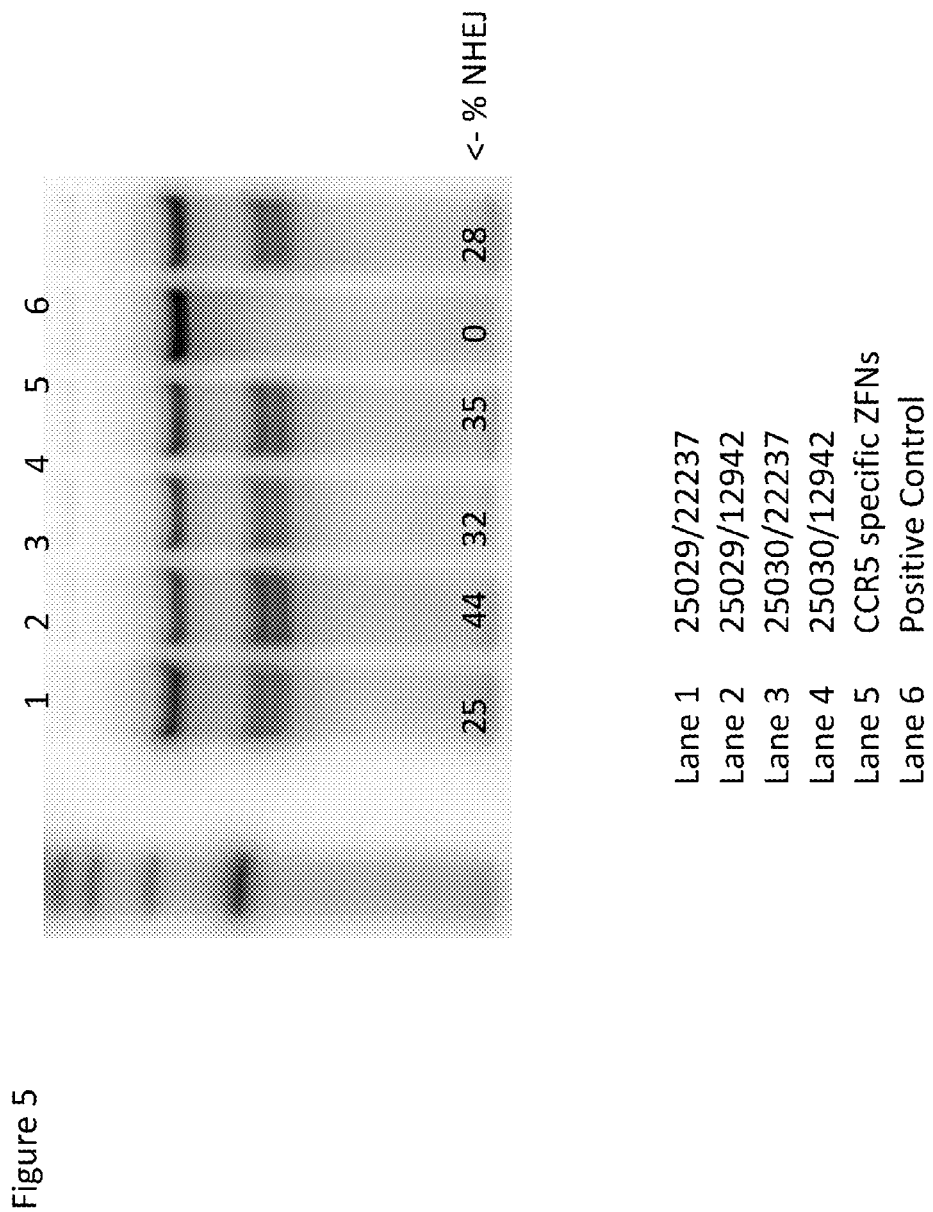
FIG. 5 depicts the results for the PD1 specific ZFN pairs tested in CD4+ T cells and analyzed using the Cel-I assay for genome editing activity. In these cells, up to 44% editing was observed with some pairs.

The PD1 specific ZFN pairs that had been further elaborated were tested in CD4+ T cells as described above in Example 1. As seen in FIG. 5, up to 44% editing was observed with some pairs. In this experiment, 'Positive Control' indicates cutting using the 25025/12942 ZFN pair in CD8+ T cells performed previously under different experimental conditions.

One lead pair, 25029/12942 was chosen for further use in isolating PD1 modified cells. Briefly, in these experiments, CD4+ T cells were treated with mRNA encoding the PD1 specific ZFNs, cultured under the "30 degree" conditions and then stimulated with a first exposure to anti-CD3/CD8 beads (Dynal) as described above in Example 1, which stimulates strong expression of the ZFN transgenes and promotes cleavage at the PD1 locus (see United States Patent Publication No. 20080311095). Following this first stimulation, the cells were re-stimulated and subjected to a purification procedure, either by FACs or by affinity chromatography.

Briefly, the CD4+ T cells were treated either with CCR5-specific ZFNs (see United States Patent Publication 20080159996) or the PD1-specific ZFNs. Cells were collected and analyzed for PD1 editing by the Cel-I assay (described above), i) following the first stimulation, ii) following the second stimulation but prior to any purification, iii) following cell sorting for CD25+ (a marker of activation), PD1(−) using standard methodology, or iv) after affinity chromatography using a matrix made with either anti-PD1 antibody or anti-CD25 antibody.

As shown in FIG. 6, using the cell sorting technique (where cells were isolated that were positive for CD25 but negative for PD1), up to 56% of the recovered cells were found to be modified as assayed by the Cel-I assay. PD1(−) cells purified by the affinity chromatography technique (where cells were subjected to affinity matrices made using

TABLE 7

| | PD1 expression and viability in TILs | | | | | |
|---|---|---|---|---|---|---|
| | CD3 stimulation | | | Tumor extracts | | |
| | GFP | 12942 EL/12947 KK | 12942/12947 | GFP | 12942 EL/12947 KK | 12942/12947 |
| PD1 expression | 32.2% | 31.5% | 14.1% | 22.9% | 13.8% | 7.5% |
| % viability TIL | 30.3% | 34.2% | 45.6% | 18% | 32% | 47.9% |
| % viability tumor cell | N/A | N/A | N/A | 45.7% | 33.1% | 19.6% |
| % PD1 + divided cells | 1.6% | 0.9% | 0.3% | 1.1% | 0.3% | 0.1% |
| % PD1 − divided cells | 3.9% | 3.0% | 2.1% | 3.0% | 1.4% | 0.8% |

The data in Table 7 demonstrate that when cells are stimulated by anti-CD3 antibodies, decreased PD1 expression, through the action of the PD1 specific ZFNs, leads to increased cell viability. When the transduced cells are treated with tumors, the same phenomenon is observed—the either anti-PD1 antibodies, anti-CD25 antibodies, or both) displayed an overall PC1 modification of up to 42% as assayed by Cel-1 analysis.

Cells that had been purified by cell sorting were also analyzed at their PD1 locus by sequencing, and the results are presented below in Table 8. As can be seen from the table, the percent target modification ("% NHEJ") predicted by the Cel-I analysis is similar to that found by the sequencing analysis. In this table, the 'Sample' label corresponds to those shown in FIG. 6.

TABLE 8

Percent PD1 modification in CD25+ cells

| Sample | % NHEJ by Cel I | % NHEJ by sequencing | Number modified* | insertions | deletions |
| --- | --- | --- | --- | --- | --- |
| 4 | 43 | 62 | 54 of 87 | 3 of 54 | 51 of 54 |
| 8 | 56 | 81 | 65 of 80 | 4 of 65 | 61 of 65 |
| 13 | 42 | 59 | 43 of 73 | 1 of 43 | 42 of 43 |

*'Number modified' indicates the number of sequences in the sequencing group that were observed to be modified. For example, in sample 4, 54 sequences of the 87 analyzed were modified.

The PD1 specific ZFNs were also tested in CD8+ T cells. In this experiment, mRNAs encoding the PD1 specific ZFNs were produced using the Ribomax Large Scale RNA ProductionT7 kit (Promega), followed by the RNeasy mini kit (Qiagen), both according to the manufacturer's protocols. Varying amounts of mRNAs were used to transduce the cells using the Amaxa Nucleofection delivery system as described above, and the percent PD1 modification was analyzed by the Cel I assay.

As shown in FIG. 7, the amount of modification observed, as described as '% NHEJ', is related to the amount of mRNA used, with lesser amounts of input mRNA resulting in lesser percentages of target modification.

These results demonstrate that the PD1 specific ZFNs described herein are capable of modifying the PD1 locus in cell lines and in primary T cells.

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. A method of activating PD1 expression in a human subject having an autoimmune disease or disorder, the method comprising
activating expression of the PD1 gene in an isolated T cell by administering a polynucleotide encoding a fusion protein comprising a zinc finger protein and a transcriptional activation domain to the cell, wherein the zinc finger protein comprises comprising four, five or six zinc finger recognition regions ordered from F1 to F4, F1 to F5 or F1 to F6, from N-terminus to C-terminus, and wherein the recognition regions comprise the following amino acid sequences:

(i) F1: QSGHLSR (SEQ ID NO: 1), F2: RSDSLSV (SEQ ID NO: 2), F3: HNDSRKN (SEQ ID NO: 3), F4: RSDDLTR (SEQ ID NO: 4), and F5: RSDHLTQ (SEQ ID NO: 5);

(ii) F1: RSAALSR (SEQ ID NO: 6), F2: RSDDLTR (SEQ ID NO: 4), F3: RSDHLTT (SEQ ID NO: 7), F4: DRSALSR (SEQ ID NO: 8), and F5: DRSALAR (SEQ ID NO: 9);

(iii) F1: RSAALAR (SEQ ID NO: 10), F2: RSDDLSK (SEQ ID NO: 11), F3: RNDHRKN (SEQ ID NO: 12), F4: DRSALSR (SEQ ID NO: 8), and F5: DRSALAR (SEQ ID NO: 9);

(iv) F1: RSDHLSE (SEQ ID NO: 13), F2: TSSDRTK (SEQ ID NO: 14), F3: RSDHLSE (SEQ ID NO: 13), and F4: QSASRKN (SEQ ID NO: 15);

(v) F1: RSDVLSE (SEQ ID NO: 16), F2: RSANLTR (SEQ ID NO: 17), F3: RSDHLSQ (SEQ ID NO: 18), F4: TSSNRKT (SEQ ID NO: 19), F5: DRSNLSR (SEQ ID NO: 20), and F6: RSDALAR (SEQ ID NO: 21); or (vi) F1: DDWNLSQ (SEQ ID NO: 22), F2: RSANLTR (SEQ ID NO: 17), F3: RSDHLSQ (SEQ ID NO: 18), F4: TSSNRKT (SEQ ID NO: 19), F5: DRSNLSR (SEQ ID NO: 20), and F6: RSDALAR (SEQ ID NO: 21);

(vii) F1: RSSALSR (SEQ ID NO: 23), F2: RPLALKH (SEQ ID NO: 24), F3: RNDHRKN (SEQ ID NO: 12), F4: TRPVLKR (SEQ ID NO: 25), and F5: DRSALAR (SEQ ID NO: 9);

(viii) F1: QSGHLSR (SEQ ID NO: 1), F2: RSDSLSV (SEQ ID NO: 2), F3: HNDSRKN (SEQ ID NO: 3), F4: RANSLLR (SEQ ID NO: 26), and F5: RSDHLTQ (SEQ ID NO: 5);

(ix) F1: RPSTLHR (SEQ ID NO: 27), F2: RSDELTR (SEQ ID NO: 28), F3: RNNNLRT (SEQ ID NO: 29), F4: TRPVLKR (SEQ ID NO: 25), and F5: DRSALAR (SEQ ID NO: 9);

(x) F1: RPSTLHR (SEQ ID NO: 27), F2: RSDELTR (SEQ ID NO: 28), F3: TNWHLRT (SEQ ID NO: 30), F4: TRPVLKR (SEQ ID NO: 25), and F5: DRSALAR (SEQ ID NO: 9);

(xi) F1: RPSTLHR (SEQ ID NO: 27), F2: RSDELTR (SEQ ID NO: 28), F3: RTPHLTL (SEQ ID NO: 31), F4: TRPVLKR (SEQ ID NO: 25), and F5: DRSALAR (SEQ ID NO: 9);

(xii) F1: RPSTLHR (SEQ ID NO: 27), F2: RSDELTR (SEQ ID NO: 28), F3: RSAQLAT (SEQ ID NO: 32), F4: TRPVLKR (SEQ ID NO: 25), and F5: DRSALAR (SEQ ID NO: 9);

(xiii) F1: RPSTLHR (SEQ ID NO: 27), F2: RSDELTR (SEQ ID NO: 28), F3: RCTHLYL (SEQ ID NO: 33), F4: TRPVLKR (SEQ ID NO: 25), and F5: DRSALAR (SEQ ID NO: 9);

(xiv) F1: RPSTLHR (SEQ ID NO: 27), F2: RSDELTR (SEQ ID NO: 28), F3: RPTQRYS (SEQ ID NO: 34), F4: TRPVLKR (SEQ ID NO: 25), and F5: DRSALAR (SEQ ID NO: 9);

(xiv) F1: RPSTLHR (SEQ ID NO: 27), F2: RSDELTR (SEQ ID NO: 28), F3: RANHREC (SEQ ID NO: 35), F4: TRPVLKR (SEQ ID NO: 25), and F5: DRSALAR (SEQ ID NO: 9);

(xvi) F1: RKFARPS (SEQ ID NO: 36), F2: RNFSRSD (SEQ ID NO: 37), F3: HPHHRMC (SEQ ID NO: 38), F4: TRPVLKR (SEQ ID NO: 25), and F5: DRSALAR (SEQ ID NO: 9);

(xvii) F1: RPSTLHR (SEQ ID NO: 27), F2: RSDELTR (SEQ ID NO: 28), F3: RMGRLST (SEQ ID NO: 39), F4: TRPVLKR (SEQ ID NO: 25), and F5: DRSALAR (SEQ ID NO: 9);

(xviii) F1: RPSTLHR (SEQ ID NO: 27), F2: RSDELTR (SEQ ID NO: 28), F3: RHSRLTT (SEQ ID NO: 40), F4: TRPVLMR (SEQ ID NO: 41), and F5: DRSALAR (SEQ ID NO: 9);

(xix) F1: RPSTLHR (SEQ ID NO: 27), F2: RSDELTR (SEQ ID NO: 28), F3: RANHRVC (SEQ ID NO: 42), F4: TRPVLKR (SEQ ID NO: 25), and F5: DRSALAR (SEQ ID NO: 9);

(xx) F1: RPSTLHR (SEQ ID NO: 27), F2: RSDELTR (SEQ ID NO: 28), F3: RSTHLLG (SEQ ID NO: 43), F4: TRPVLKR (SEQ ID NO: 25), and F5: DRSALAR (SEQ ID NO: 9);

(xxi) F1: RNAALTR (SEQ ID NO: 45), F2: RSDELTR (SEQ ID NO: 28) F3: RSCGLWS (SEQ ID NO: 44), F4: TRPVLKR (SEQ ID NO: 25), and F5: DRSALAR (SEQ ID NO: 9);

(xxii) F1: CNAALTR (SEQ ID NO: 46), F2: RSDELTR (SEQ ID NO: 28), F3: REEHRAT (SEQ ID NO: 47), F4: TRPVLKR (SEQ ID NO: 25), and F5: DRSALAR (SEQ ID NO: 9);

(xxiii) F1: RNAALTR (SEQ ID NO: 45), F2: RSDELTR (SEQ ID NO: 28), F3: RHHHLAA (SEQ ID NO: 48), F4: TRPVLKR (SEQ ID NO: 25), and F5: DRSALAR (SEQ ID NO: 9);

(xxiv) F1: RNAALTR (SEQ ID NO: 45), F2: RSDELTR (SEQ ID NO: 28), F3: RPMHLTN (SEQ ID NO: 49), F4: TRPVLKR (SEQ ID NO: 25), and F5: DRSALAR (SEQ ID NO: 9);

(xxv) F1: RNAALTR (SEQ ID NO: 45), F2: RSDELTR (SEQ ID NO: 28), F3: RSPHLYH (SEQ ID NO: 50), F4: TRPVLKR (SEQ ID NO: 25), and F5: DRSALAR (SEQ ID NO: 9);

(xxvi) F1: RNAALTR (SEQ ID NO: 45), F2: RSDELTR (SEQ ID NO: 28), F3: RCEALHH (SEQ ID NO: 51), F4: TRPVLKR (SEQ ID NO: 25), and F5: DRSAQAR (SEQ ID NO: 52);

(xxvii) F1: RNAALTR (SEQ ID NO: 45), F2: RSDELTR (SEQ ID NO: 28), F3: RCEALHH (SEQ ID NO: 51), F4: TRPVLKR (SEQ ID NO: 25), and F5: DRSALAR (SEQ ID NO: 9);

(xxviii) F1: RNAALTR (SEQ ID NO: 45), F2: RSDELTR (SEQ ID NO: 28), F3: RLPALLS (SEQ ID NO: 53), F4: TRPVLKR (SEQ ID NO: 25), and F5: DRSALAR (SEQ ID NO: 9); and (xxix) F1: HNAALTR (SEQ ID NO: 54), F2: RSDELTR (SEQ ID NO: 28), F3: RTYNRTQ (SEQ ID NO: 55), F4: TRPVLKR (SEQ ID NO: 25), and F5: DRSALAR (SEQ ID NO: 9) and administering the T cell to the human subject.

2. The method of claim 1, wherein the autoimmune disease is Hashimoto's thyroiditis, Systemic lupus erythematosus, Sjogren's syndrome, Graves' disease, Scleroderma, Rheumatoid arthritis, Multiple sclerosis, Myasthenia gravis and/or Diabetes.

3. The method of claim 1, wherein the cell is a CD4+ T-cell.

* * * * *